United States Patent [19]
Rivier

[11] Patent Number: 5,844,074
[45] Date of Patent: Dec. 1, 1998

[54] CYCLIC CRF AGONISTS

[75] Inventor: Jean E. F. Rivier, La Jolla, Calif.

[73] Assignee: The Salk Institute for Biological Studies, San Diego, Calif.

[21] Appl. No.: 575,148

[22] Filed: Dec. 19, 1995

Related U.S. Application Data

[63] Continuation-in-part of Ser. No. 353,928, Dec. 12, 1994, Pat. No. 5,663,292.

[51] Int. Cl.$^6$ .......................... A61K 38/28; A61K 38/12; C07K 14/695; C07K 7/64
[52] U.S. Cl. .......................... 530/306; 530/317; 930/21; 930/70; 930/260; 514/9; 514/2; 514/805
[58] Field of Search ........................... 530/306, 317; 514/9, 2, 805; 930/21, 70, 260

[56] References Cited

U.S. PATENT DOCUMENTS

| | | | |
|---|---|---|---|
| 5,439,885 | 8/1995 | Kornreich et al. | 514/12 |
| 5,493,006 | 2/1996 | de Miranda et al. | 530/306 |

OTHER PUBLICATIONS

Gulyas et al., "Potent, structurally constrained agonists and competitive antagonists of corticotropin–releasing factor", *P.N.A.S.*, vol. 92, pp. 10575–10579 (Nov. 1995).

Miranda, A. et al. Conformationally restricted competitive a factor. J. Med. Chem. 37, 1450–1459, Oct. 1994.

*Primary Examiner*—Cecilia J. Tsang
*Assistant Examiner*—Michael Borin
*Attorney, Agent, or Firm*—Fitch, Even, Tabin & Flannery

[57] ABSTRACT

Novel cyclic CRF agonist peptides have the amino acid sequence: (cyclo 30-33)Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln-$R_{30}$-Ala-$R_{32}$-$R_{33}$-Asn-Arg-Lys-Leu-Nle-Glu-Ile-Ile-$NH_2$ wherein $R_{30}$ is Glu or Cys; $R_{32}$ is His or a D-amino acid such as D-His, D-Arg or similar; $R_{33}$ is Lys, Orn or Cys. The N-terminus may be extended by Ser-Glu-Glu. Lys may be substituted for $Arg^{23}$, and its side chain connected by a lactam bridge to $Glu^{20}$ to form a bicyclic peptide. Certain disclosed CRF agonists include:

(cyclo 30-33)[Ac-$Pro^4$, D-$Phe^{12}$, $Nle^{21,38}$, D-$His^{32}$, $Glu^{30}$, $Lys^{33}$]r/hCRF(4-41), (cyclo 30-33)[Ac-$Pro^4$, D-$Phe^{12}$, $Nle^{21,38}$, D-$His^{32}$, $Glu^{30}$, $Orn^{33}$]r/hCRF(4-41), (cyclo 30-33)[Ac-$Pro^4$, D-$Phe^{12}$, $Nle^{21,38}$, $Cys^{30,33}$, D-$His^{32}$]r/hCRF(4-41), (bicyclo 20-23,30-33)[Ac-$Pro^4$, D-$Phe^{12}$, $Nle^{21,38}$, $Lys^{23,33}$, $Glu^{30}$, D-$His^{32}$]-r/hCRF(4-41), (cyclo 30-33)[Ac-$Pro^4$, D-$Phe^{12}$, $Nle^{21,38}$, $CML^{27}$, $Glu^{30}$, imBzlD-$His^{32}$, $Lys^{33}$]r/hCRF(4-41) and (cyclo 30-33)[Ac-$Pro^4$, D-$Phe^{12}$, $Nle^{21,38}$, $Glu^{30}$, D-$Arg^{32}$, $Lys^{33}$]r/hCRF(4-41).

Labelled agonists such as (cyclo 30-33)[$I^{125}Tyr^o$, D-$Phe^{12}$, $Nle^{21,38}$, $Glu^{30}$, D-$His^{32}$, $Lys^{33}$]r/hCRF and (cyclo 30-33) [$I^{125}$D-$Tyr^3$, D-$Phe^{12}$, $Nle^{21,38}$, $Glu^{30}$, D-$His^{32}$, $Lys^{33}$]r/hCRF(3-41) are useful in screening for more potent agonists.

20 Claims, No Drawings

CYCLIC CRF AGONISTS

This application is a continuation-in-part of my earlier application Ser. No. 08/353,928 filed Dec. 12, 1994, now U.S. Pat. No. 5,663,292.

This invention was made with Government support under grant number DK-26741 awarded by the National Institutes of Health. The Government has certain rights in this invention.

This invention is generally directed to peptides and to the pharmaceutical treatment of mammals using such peptides. More specifically, the invention relates to cyclic agonists of the hentetracontapeptide CRF which mimic the pharmacological properties thereof and are superior thereto in at least some aspects, to pharmaceutical compositions containing such cyclic CRF agonists, to methods of treatment of mammals using such cyclic CRF agonists, and to methods of screening for new drugs using such peptides.

BACKGROUND OF THE INVENTION

Experimental and clinical observations have supported the concept that the hypothalamus plays a key role in the regulation of adenohypophysial corticotropic cells' secretory functions. Over 40 years ago it was demonstrated that factors present in the hypothalamus would increase the rate of ACTH secretion by the pituitary gland when incubated in vitro or maintained in an organ culture. However, a physiologic corticotropin releasing factor (CRF) was not characterized until ovine CRF (oCRF) was characterized in 1981. As disclosed in U.S. Pat. No. 4,415,558, oCRF was found to be a 41-residue amidated peptide. oCRF lowers blood pressure in mammals when injected peripherally and stimulates the secretion of ACTH and β-endorphin.

Although originally isolated and characterized on the basis of its role in this hypothalamopituitary-adrenal (HPA) axis, CRF has been found to be distributed broadly throughout the central nervous system as well as in extraneural tissues, such as the adrenal glands, placenta and testes, where it may also act as a paracrine regulator or a neurotransmitter. Moreover, the likely involvement of CRF in affective disorders, such as anxiety, depression, alcoholism and anorexia nervosa, and in modulating reproduction and immune responses suggests that changes in CRF expression may have important physiological and pathophysiological consequences. For example, perturbations in the regulatory loops comprising the HPA axis often produce chronically elevated levels of circulating glucocorticoids; such patients display the physical hallmarks of Cushing's syndrome, including truncal obesity, muscle-wasting, and reduced fertility.

In addition to its role in mediating activation of the hypothalamic-pituitary-adrenal, CRF has also been shown to modulate autonomic and behavioral changes, some of which occur during the stress response. Many of these behavioral changes have been shown to occur independently. of HPA activation in that they are not duplicated by dexamethasone treatment and are insensitive to hypophysectomy. In addition, direct infusion of CRF into the CNS mimics autonomic and behavioral responses to a variety of stressors. Because peripheral administration of CRF or a CRF antagonist fails to affect certain of these changes, it appears that CRF exhibits a direct brain action with respect to such functions, which include appetite suppression, increased arousal and learning ability.

As a result of the extensive anatomical distribution and multiple biological actions of CRF, this regulatory peptide is believed to be involved in the regulation of numerous biological processes. CRF has also been implicated in the regulation of inflammatory responses. Although it has been observed that CRF plays a pro-inflammatory role in certain animal models, CRF appears to suppress inflammation in others by reducing injury-induced increases in vascular permeability.

In about 1981, a 40-residue amidated peptide generally similar to CRF was isolated from the skin of the South American frog *Phyllomedusa sauvagei*; it is referred to as sauvagine. It was characterized by Erspamer et al. and was described in *Regulatory Peptides*, Vol. 2 (1981), pp. 1–13. Sauvagine has an amino acid sequence homologous to ovine CRF. When given intravenously (iv), sauvagine and oCRF have been reported to cause vasodilation of the mesenteric arteries so as to lower blood pressure in mammals and also in stimulating the secretion of ACTH and β-endorphin. However, when administered intracerebroventricularly (icv), there is an elevation of heart rate and mean arterial blood pressure, which are secondary to activation of the sympathetic nervous system.

Rat CRF (rCRF) was later isolated, purified and. characterized; it was found to be a homologous, amidated hentetracontapeptide, as described in U.S. Pat. No. 4,489, 163, having 7 amino acid differences from oCRF. The amino acid sequence of human CRF has now been determined to be the same as that of rCRF. rCRF and hCRF are used interchangeably, and the designation r/hCRF is frequently used with respect to this peptide hormone.

At about the same time, two homologous polypeptides were isolated from the urophyses of different species of fish. These isolated peptides were generally homologous to oCRF, i.e. about 54% homology, and were termed Urotensin I (UI). The polypeptide from the *Catostomus commersoni* (white sucker) is sometimes referred to as sucker fish(sf) urotensin. Its purification and characterization are described in an article by Lederis et al., *Science* Vol. 218, No. 4568, 162–164 (Oct. 8, 1982). A homolog, carp urotensin, was obtained from *Cyprinus carpio* and is described in U.S. Pat. No. 4,533,654.

Another urotensin having a homologous amino acid sequence was later isolated from the urophyses of *Hippoglossoides elassodon* or Flathead (Maggy) Sole; it is sometimes referred to as Maggy urotensin and is described in U.S. Pat. No. 4,908,352. Synthetic UIs have been found to also stimulate ACTH and β-endorphin activities in vitro and in vivo and to have many of the same general biological activities of CRFs and sauvagine.

Since the original discoveries of CRFs in mammals and urotensins in fish, CRFs have now been shown to exist in other animal species. For example, fish CRF was found to be a 41-residue peptide having high homology to r/hCRF; it is described in an article by Lederis et al. that appears at pages 67–100 in *Fish Physiology* (ed. Farrell), Academic Press, San Diego, 1994). Synthetic fish CRF (fCRF) stimulates ACTH and β-endorphin activities in vitro and in vivo and has similar biological activities to mammalian CRFs. These various CRFs and urotensins, along with sauvagine are considered to form a larger family of CRF-like peptides and analogs.

One such CRF analog having a high alpha-helical forming potential was developed in about early 1984. It is a 41-residue amidated peptide commonly referred to as AHC (alpha-helical CRF) and is described in U.S. Pat. No. 4,594,329. Other CRF analogs containing D-isomers of α-amino acids were developed, such as those shown in U.S.

Pat. No. 5,278,146. Synthetic r/hCRF, oCRF and AHC all stimulate ACTH and β-endorphin-like activities (β-END-Li) in vitro and in vivo and substantially lower blood pressure when injected peripherally. Biopotent cyclic CRF analogs are disclosed in U.S. Pat. No. 5,245,009 (Sep. 14, 1993) and in allowed U.S. Pat. application Ser. No. 78,558, filed Jun. 16, 1993, now U.S. Pat. No. 5,493,006.

Since the foregoing discoveries, the search for improved CRF agonists has continued.

SUMMARY OF THE INVENTION

Cyclic analogs of this CRF family of peptides have now been discovered which exhibit longer lasting and improved biological activity. It is shown that any of the members of the family of CRF-like peptides can be modified to create highly biopotent CRF agonists that bind strongly to the known CRF receptors and activate the CRF receptors. The CRF family is considered to encompass those peptides which bind to the CRF receptors and have at least about 45% amino acid structural homology with ovine CRF, the first mammalian CRF isolated and characterized. The CRF family includes, but is not limited to, the following known peptides: ovine CRF, rat/human CRF, porcine CRF, bovine CRF, fish CRF, α-helical CRF(AHC), carp urotensin, sucker urotensin, maggy urotensin, flounder urotensin, sole urotensin and sauvagine. These modifications incorporate a cyclizing bond, preferably a lactam, within the molecule which joins the side chains of the residues that are located as the 8th and 11th residues from the C-terminal residue, e.g. (cyclo 30-33) [$Glu^{30}$, $Lys^{33}$]r/hCRF, and also incorporate a D-isomer, preferably a residue of a basic or aromatic amino acid, as the residue which is the 9th residue from the C-terminal residue, e.g. (cyclo 30-33)[$Glu^{30}$, $D-His^{32}$, $Lys^{33}$]-r/hCRF.

Such CRF agonist peptides are identified by the following general formula: A-$Xaa_c$-Xaa-D-Xaa-$Xaa_c$-B-$NH_2$ wherein A is a sequence of 26 to 29 amino acid residues of the complete or a shortened N-terminal portion of a selected peptide of the CRF family; $Xaa_c$ are amino acid residues the side chains of which are linked in a cyclizing bond; Xaa is a natural α-amino acid residue other than Cys and preferably one, such as Ala, which occupies this position in the sequence of this selected member of the CRF family; D-Xaa is a D-isomer amino acid, i.e. a D-isomer of an unnatural α-amino acid or of a natural α-amino acid other than Cys, preferably one that is aromatic and/or basic, and B is a sequence of the last 8 amino acid residues of the C-terminal portion of this selected peptide of the CRF family. The N-terminus may be acylated as is known in this art of CRF analogs. Thus, it can be seen that such peptides are modified versions of the 40- or 41-residue sequence of a CRF family peptide, which can be shortened by the deletion of 1, 2 or 3 residues beginning at the N-terminus thereof. Additional substitutions such as are presently well known in the field of CRF agonists, as a result of having been developed over the last decade, may also be made in these modified cyclic peptides, e.g. the substitution of Met or Leu by Nle and/or the substitution of D-Phe or D-Leu into the 12-position of the 41-residue peptide or into the 11-position of the 40-residue peptide, i.e. at a position spaced 19 residues from D-Xaa.

More specifically, these CRF agonists have a cyclizing bond between the residues in the 30- and 33-positions, and they may optionally have a second such bond between the residues in the 20- and 23-positions. Either or both of these bonds may be a disulfide linkage between two Cys residues, but they are preferably each an amide bond (i.e. a lactam bridge) between side chain carboxyl and amino groups. Most preferably, there is a lactam bridge between a side chain carboxyl group on the residue in the 30-position, preferably Glu, and a side chain amino group on the 33-position residue, preferably Lys or Orn. Also the naturally occurring residues of the CRF-like family may be present in this position which corresponds to the 32-position of CRF, i.e. His, Gly, Leu, Gln and Ala; but any α-amino acid is tolerated here. However, there is preferably a basic and/or aromatic D-isomer residue or an equivalent in the 32-position in the region between the residues joined by this lactam bridge, e.g. D-His, D-Arg, D-Tyr, D-Nal, D-Pal, D-Dpr(Nic), D-Dpr(isopropyl), D-Aph, D-Amp, D-Iamp, D-Har, D-Agl(Nic), D-Lys(isopropyl), D-Orn, D-Dbu, D-Dpr, D-Hly, D-Hly(Nic), D-Orn(Nic), D-Orn(isopropyl), D-(alkyl)Arg, D-(dialkyl)Arg, D-Lys(Nic), imBzlD-His, D-(dialkyl)Har or a comparable D-isomer. However, a wide variety of other residues such as D-Ala, D-Glu, D-Asn, Aib, Asn, Pal, Nal, Phe and Tyr may also be present. D-His, D-Arg, D-Pal, D-Amp, D-Iamp or D-2Nal is particularly preferred in the 32-position. When the second cyclizing bond option is incorporated, a lactam bridge between Glu in the 20-position and Lys in the 23-position is most preferred, and a D-isomer may also be optionally included in the 22-position. When the second lactam bridge is not included, D-Glu may be substituted in the 20-position.

These CRF agonists also have the preferred optional substitutions of D-Phe, D-Tyr or D-Leu or an equivalent D-isomer, e.g. D-Cpa, D-2Nal or D-3Pal, in the 12-position and norleucine substituted for any naturally occurring Met, e.g. in the 21 and 38 positions. The N-terminus may be shortened by elimination of residues N-terminally of the Pro-Pro dipeptide residue; for example Ser, Ser-Glu or Ser-Glu-Glu can be eliminated from the N-terminus of r/hCRF. When such shortening occurs, the N-terminus is preferably acylated. Tyr or D-Tyr may also be added at the N-terminus if desired to facilitate labeling by radioiodination. When D-Tyr is to be radioiodinated, it may be preferable to substitute Asn, D-Asn or D-Ala for $His^{32}$ or $D-His^{32}$ and Arg for $Lys^{36}$ as they are generally considered to be structural equivalents which may be more stable. D-Pro may be substituted for either $Pro^4$ or $Pro^5$, and analogs with $D-Pro^5$ have advantageous anti-inflammatory properties. Other optional substitutions may also be made throughout the molecule as previously taught, and these are considered to be functional equivalents of the specific peptides described hereinafter. For example, the Leu residue in the 27-position can be substituted with a methyl group on its α-carbon atom, i.e., CML, and $CML^{27}$ is preferred. Other Leu residues throughout the CRF molecule, e.g. at positions- 14, -15, -19 and -37 may optionally be substituted by CML, and $CML^{17}$ may also be present. Such other substitutions, both alone and in combination with the aforementioned substitutions, are considered to enhance biopotency and/or to increase duration of action, but their individual effect appears to be far less than that of either the 30-33 side chain bridge or the combination of such bridge with the appropriate D-isomer in the 32-position. Although these cyclic CRF agonists may be further shortened by elimination of one or both of the Pro residues, the Pro-Pro dipeptide, either with or without one optional D-Pro substitution, is preferably included at such an N-terminus. Overall, the CRF cyclic agonists disclosed herein all include at least one D-isomer residue.

Pharmaceutical compositions in accordance with the invention include such CRF agonists, or nontoxic addition salts thereof that are dispersed in a pharmaceutically acceptable liquid or solid carrier. The administration of such peptides or pharmaceutically acceptable addition salts thereof to mammals, particularly humans, in accordance with the invention may be carried out for the regulation of secretion of ACTH, β-endorphin, β-lipotropin, corticosterone and other products of the pro-opiomelanocortin (POMC) gene and corticosterone and/or for lowering blood pressure or increasing coronary flow and/or decreasing swelling and inflammation and/or for affecting learning, mood, behavior, appetite, gastrointestinal and intestinal functions and autonomic nervous system activities.

The peptides may also be used for drug screening for even more potent CRF agonists which bind to and activate CRF receptors.

DETAILED DESCRIPTION OF THE PREFERRED EMBODIMENTS

The nomenclature used to define the peptides is that specified by Schroder & Lubke, "The Peptides", Academic Press (1965) wherein, in accordance with conventional representation, the amino group appears to the left and the carboxyl group to the right. The standard 3-letter abbreviations are used to identify the alpha-amino acid residues, and where the amino acid residue has isomeric forms, it is the L-form of the amino acid that is represented unless otherwise expressly indicated, e.g. Ser=L-serine. In addition the following abbreviations are used: Orn=ornithine, Nle=norleucine, Nva=norvaline, Agl=aminoglycine, Abu=2-aminobutyric acid, Dbu=2,4-diaminobutyric acid, Dpr=2,3-diaminopropionic acid, Hly=homolysine, Har=homoarginine, CML=$C^\alpha CH_3$-leucine; Aib=$C^\alpha CH_3$-L-alanine or 2-aminoisobutyric acid; Nal=L-β-(1- or 2-naphthyl)alanine; Pal=L-β-(2-, 3- or 4-pyridyl)alanine; Cpa=L-(2-, 3-, or 4-chloro) phenylalanine; Aph=L-(2-, 3- or 4-amino)phenylalanine; Amp=(2-, 3- or 4-aminomethyl) phenylalanine; Iamp=isopropyl Amp; imBzlHis=imidazolebenzyl Histidine; Nic=3-carboxypyridine (or nicotinic acid); Nph=naphthoyl and Flu=fluorenoyl.

Generally, the CRF agonists are most broadly identified by the formula:
A-$Xaa_c$-Xaa-D-Xaa-$Xaa_c$-B-$NH_2$ wherein A is a sequence of 26 to 29 amino acid residues of the corresponding portion of a selected peptide of the CRF family; $Xaa_c$ are amino acid residues the side chains of which are linked in a cyclizing bond; Xaa is a natural α-amino acid residue other than Cys and preferably one, such as Ala, which occupies this position in the sequence of this selected member of the CRF family; D-Xaa is a D-isomer α-amino acid, i.e. a D-isomer of an unnatural α-amino acid or a natural α-amino acid other than Cys, preferably one that is aromatic and/or basic, and B is a sequence of the last 8 amino acid residues of the C-terminal portion of this selected peptide of the CRF family. They preferably also include a D-isomer in the 12-position of the CRF analog or the corresponding 11-position of a 40-residue native peptide. D-Pro may be substituted in either the 4- or the 5-position. The N-terminus may be acylated, and/or D-Tyr or Tyr may be added, e.g. to facilitate labelling. Most preferably they have an acylated N-terminus which is shortened to begin with the Pro-Pro dipeptide, and they include a D-isomer in the 32-position. Optional D-isomer substitutions may be made in the 20- and 22-positions.

One broad group of CRF agonists is defined by the following amino acid sequence (which should be understood to include the equivalent nontoxic salts thereof) and is based upon substitution of residues at particular positions that have been shown to be permitted in the CRF family sequence without impairing CRF biopotency:

(cyclo 30-33)$Y_1$-$Y_2$-Pro-Pro-$R_6$-Ser-$R_8$-Asp-Leu-$R_{11}$-D-Phe-$R_{13}$-$R_{14}$-$R_{15}$-Arg-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$ -$R_{32}$-$R_{33}$-$R_{34}$-Arg-$R_{36}$-$R_{37}$-$R_{38}$-$R_{39}$-$R_{41}$-$NH_2$ wherein $Y_1$ is H or an acylating agent having up to 15 carbon atoms but preferably up to 7 carbon atoms, e.g. Ac, Fr, Acr, Bz, Nph or Flu; $Y_2$ is Glu, Asp, Gly, Glu-Glu, Asn-Asp, Gln-Glu, pGlu-Gly, Ser-Glu-Glu, Asn-Asp-Asp, Ser-Gln-Glu, or des-$Y_2$; $R_6$ is Ile, Met or Nle; $R_8$ is Leu or Ile; $R_{11}$ is Thr or Ser; $R_{13}$ is His, Tyr or Glu; $R_{14}$ is CML or Leu; $R_{15}$ is CML or Leu; $R_{17}$ is Glu, CML, Asn or Lys; $R_{18}$ is Val, Nle or Met; $R_{19}$ is CML, Leu, Ile, Ala or Aib; $R_{20}$ is Glu, D-Glu, Cys or His; $R_{21}$ is Nle, Ile or Met; $R_{22}$ is Ala, D-Ala, Aib, Thr, Asp or Glu; $R_{23}$ is Arg, Cys, Orn or Lys; $R_{24}$ is Ala, Gln, Ile, Asn or Aib; $R_{25}$ is Asp or Glu; $R_{26}$ is Gln, Asn or Lys; $R_{27}$ is CML, Glu, Gln or Leu; $R_{28}$ is Ala, Lys, Arg or Aib; $R_{29}$ is Gln, Aib or Glu; $R_{30}$ is Glu or Cys; $R_{31}$ is Ala or Aib; $R_{32}$ is His or D-His or an equivalent L-isomer or D-isomer α-amino acid, examples of which are set forth below; $R_{33}$ is Lys, Orn or Cys; $R_{34}$ is Asn or Aib; $R_{36}$ is Lys, Orn, Arg, Har or Leu; $R_{37}$ is CML, Leu, Nle or Tyr; $R_{38}$ is Nle, Met or Leu; $R_{39}$ is Glu, Aib or Asp; $R_{40}$ is Ile, Aib, Thr, Glu, Ala, Val, Leu, Nle, Phe, Nva, Gly or Gln; and $R_{41}$ is Ala, Ile, Gly, Val, Leu, Nle, Phe, Nva or Gln; wherein Tyr or D-Tyr may be optionally included at the N-terminus; and wherein D-Phe may be substituted by Phe, Leu or Tyr or another D-isomer α-amino acid, such as D-Leu, D-Tyr, D-Cpa, D-Nal or D-Pal, and wherein either $Pro^4$ or $Pro^5$ may be substituted by D-Pro; provided that when $R_{30}$ is Glu, $R_{33}$ is Lys or Orn and when $R_{30}$ is Cys, $R_{33}$ is Cys; and provided further that a second cyclizing bond may exist between $R_{20}$ and $R_{23}$. As an alternative to such optional acylation at the N-terminus, a sulfonamide may be formed, or a sugar or a lipid can be added to modulate duration of action and solubility. As earlier indicated, there is wide latitude for selection of the residue in position-32, and examples of suitable additional residues for $R_{32}$ include the D- and L-isomers of Asn, Har, Arg, Nal, imBzlHis, Tyr, Ala, Leu, Val, Ser, Thr, Cpa, Pal, Lys, Phe and Gln, as well as Aib, Gly, D-Dpr(Nic), D-Dpr(isopropyl), D-Aph, D-Amp, D-Iamp, D-Lys(Nic), D-Agl(Nic), D-Lys (isopropyl), D-Orn, D-Dbu, D-Dpr, D-Hly, D-Hly(Nic), D-Orn(Nic), D-Orn(isopropyl), D-(alkyl)Arg, D-(dialkyl) Arg or D-(dialkyl)Har. If a second cyclizing bond is present, preferably both bonds are not Cys-Cys.

A preferred group of CRF agonists has the following amino acid sequence (including nontoxic salts thereof): (cyclo 30-33)$Y_1$-$Y_2$-Pro-Pro-$R_6$-Ser-$R_8$-Asp-Leu-$R_{11}$-D-Phe-His-Leu-Leu-Arg-Glu-$R_{18}$-Leu-$R_{20}$-Nle-$R_{22}$-$R_{23}$-Ala-$R_{25}$-Gln-Leu-Ala-$R_{29}$-$R_{30}$-Ala-$R_{32}$-$R_{33}$-$R_{34}$-Arg-$R_{36}$-Leu-Nle-$R_{39}$-$R_{40}$-$R_{41}$-$NH_2$ wherein $Y_1$ is H or an acylating agent having up to 7 carbon atoms; $Y_2$ is Glu, Asp, Gly, Glu-Glu, Asn-Asp, Gln-Glu, pGlu-Gly, Ser-Glu-Glu, Asn-Asp-Asp, Ser-Gln-Glu, or des-$Y_2$; $R_6$ is Ile, Met or Nle; $R_8$ is Leu or Ile; $R_{11}$ is Thr or Ser; $R_{18}$ is Val, Nle or Met; $R_{20}$ is Glu, D-Glu, Cys or His; $R_{22}$ is Ala or Thr; $R_{23}$ is Arg, Cys, Orn or Lys; $R_{25}$ is Asp or Glu; $R_{29}$ is Gln or Glu; $R_{30}$ is Glu or Cys; $R_{32}$ is His, D-His, D-Arg, D-Amp, D-Iamp, D-2Nal, D-Glu, D-Ala or an equivalent other D-amino acid or Ala; $R_{33}$ is Lys, Cys or Orn; $R_{34}$ is Asn or Aib; $R_{36}$ is Lys or Leu; $R_{39}$ is Glu or Asp; $R_{40}$ is Ile or Glu; and $R_{41}$ is Ile or Ala; wherein Phe may be substituted for D-Phe; wherein D-Pro may be substituted for $Pro^4$ or $Pro^5$; and wherein Tyr or D-Tyr may be optionally included at the N-terminus; provided that when $R_{30}$ is Cys, $R_{33}$ is Cys; and when $R_{30}$ is Glu, $R_{33}$ is Orn or Lys; and provided further that a second cyclizing bond may exist between $R_{20}$ and $R_{23}$.

A more preferred group of CRF agonists has the following amino acid sequence (including nontoxic salts thereof):

(cyclo 30-33)$Y_1$-$Y_2$-Pro-Pro-$R_6$-Ser-$R_8$-Asp-Leu-$R_{11}$-$R_{12}$-His-Leu-Leu-Arg-Glu-$R_{18}$-$R_{19}$-$R_{20}$-$R_{21}$-$R_{22}$-$R_{23}$-$R_{24}$-$R_{25}$-Gln-$R_{27}$-$R_{28}$-Gln-$R_{30}$-$R_{31}$-$R_{32}$-$R_{33}$-$R_{34}$-Arg-Lys-Leu-Nle-$R_{39}$-Ile-$R_{41}$-$NH_2$ wherein $Y_1$ is Ac or H; $Y_2$ is Glu, Asp, Gly, Glu-Glu, Asn-Asp, Gln-Glu, pGlu-Gly, Ser-Glu-Glu, Asn-Asp-Asp, Ser-Gln-Glu, or des-$Y_2$; $R_6$ is Ile, Met or Nle; $R_8$ is Leu or Ile; $R_{11}$ is Thr or Ser; $R_{12}$ is D-Phe or D-Tyr; $R_{18}$ is Val or Nle; $R_{19}$ is CML, Leu, Ile, Ala or Aib; $R_{20}$ is Glu, D-Glu, Cys or His; $R_{21}$ is Nle or Met; $R_{22}$ is Ala, Aib or Thr; $R_{23}$ is Arg, Cys, Orn or Lys; $R_{24}$ is Ala or Aib; $R_{25}$ is Asp or Glu; $R_{27}$ is Leu or CML; $R_{28}$ is Ala or Aib; $R_{30}$ is Glu or Cys; $R_{31}$ is Ala or Aib; $R_{32}$ is D-His, D-Amp, D-Iamp, D-Arg, D-Pal, D-2Nal, D-Ala or a D-isomer of another natural amino acid other than Cys; $R_{33}$ is Lys, Orn or Cys; $R_{34}$ is Aib or Asn; $R_{39}$ is Glu or Asp; and $R_{41}$ is Ala or Ile; wherein D-Pro can be substituted for $Pro^4$ or $Pro^5$; and wherein Tyr may be optionally included at the N-terminus; provided however that a second cyclizing bond may exist between $R_{20}$ and $R_{23}$.

Still another group of preferred CRF agonists has the following amino acid sequence (including nontoxic salts thereof): (cyclo 30-33)$Y_1$-$Y_2$-Pro-Pro-$R_6$-Ser-$R_8$-Asp-Leu-$R_{11}$-D-Phe-$R_{13}$-$R_{14}$-$R_{15}$-Arg-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-Arg-$R_{36}$-$R_{37}$-$R_{38}$-$R_{39}$-$R_{40}$-$R_{41}$-$NH_2$ wherein $Y_1$ is Ac or hydrogen; $Y_2$ is Glu, Asp, Gly, Glu-Glu, Asn-Asp, Gln-Glu, pGlu-Gly, Ser-Glu-Glu, Asn-Asp-Asp, Ser-Gln-Glu, or des-$Y_2$; $R_6$ is Ile, Met or Nle; $R_8$ is Leu or Ile; $R_{11}$ is Thr or Ser; $R_{13}$ is His, Tyr or Glu; $R_{14}$ is Leu or CML; $R_{15}$ is Leu or CML; $R_{17}$ is Glu, Lys, Asn or CML; $R_{18}$ is Val, Nle or Met; $R_{19}$ is Leu, Ile or CML; $R_{20}$ is His, D-Glu, Cys or Glu; $R_{21}$ is Nle, Met or Ile; $R_{22}$ is Ala, D-Ala, Aib, Thr, Asp or Glu; $R_{23}$ is Arg, Cys, Orn or Lys; $R_{24}$ is Ala, Asn, Gln, Ile or Aib; $R_{25}$ is Asp or Glu; $R_{26}$ is Gln, Asn or Lys; $R_{27}$ is Leu, Glu, Gln or CML; $R_{28}$ is Ala, Arg, Lys or Aib; $R_{29}$ is Gln, Aib or Glu; $R_{30}$ is Glu or Cys; $R_{31}$ is Ala or Aib; $R_{32}$ is His, D-His, Aib, D-Arg, D-2Nal, D-3Pal, D-Amp, D-Iamp, Gly, Tyr, D-Tyr, Ala, D-Ala or another aromatic D-isomer α-amino acid; $R_{33}$ is Lys, Orn or Cys; $R_{34}$ is Asn or Aib; $R_{36}$ is Lys, Orn, Arg, Har or Leu; $R_{37}$ is CML, Leu or Tyr; $R_{38}$ is Nle, Met or Leu; $R_{39}$ is Glu, Aib or Asp; $R_{40}$ is Ile, Aib, Thr, Glu, Ala, Val, Leu, Nle, Phe, Nva, Gly or Gln; and $R_{41}$ is Ala, Ile, Gly, Val, Leu, Nle, Phe, Nva or Gln; wherein D-Leu or Phe or Leu may be substituted for D-Phe; wherein D-Pro may be substituted for $Pro^4$ or $Pro^5$; and wherein Tyr or D-Tyr may be optionally included at the N-terminus; provided that when $R_{30}$ is Glu, $R_{33}$ is Lys or Orn and when $R_{30}$ is Cys, $R_{33}$ is Cys; and provided further that a second cyclizing bond may exist between $R_{20}$ and $R_{23}$.

A particularly preferred group of CRF agonists has the amino acid sequence (including nontoxic salts thereof): (cyclo 30-33)$Y_1$-$Y_2$-Pro-Pro-Ile-Ser-Leu-Asp-Leu-Thr-D-Phe-His-Leu-Leu-Arg-Glu-$R_{18}$-$R_{19}$-$R_{20}$-$R_{21}$-$R_{22}$-$R_{23}$-$R_{24}$-$R_{25}$-Gln-$R_{27}$-$R_{28}$-Gln-$R_{30}$-$R_{31}$-$R_{32}$-$R_{33}$-$R_{34}$-Arg-Lys-Leu-Nle-$R_{39}$-Ile-$R_{41}$-$NH_2$ wherein $Y_1$ is H or Ac; $Y_2$ is Glu, Glu-Glu, Gln-Glu, Ser-Glu-Glu, Ser-Gln-Glu, or des-$Y_2$; $R_{18}$ is Val or Nle; $R_{19}$ is CML, Leu, Ile, Ala or Aib; $R_{20}$ is Glu, D-Glu, Cys or His; $R_{21}$ is Nle or Met; $R_{22}$ is Ala, D-Ala, Aib or Thr; $R_{23}$ is Arg, Cys, Orn or Lys; $R_{24}$ is Ala or Aib; $R_{25}$ is Asp or Glu; $R_{27}$ is Leu or CML; $R_{28}$ is Ala or Aib; $R_{30}$ is Glu or Cys; $R_{31}$ is Ala or Aib; $R_{32}$ is D-His, D-Amp, D-Iamp, D-Pal, D-Arg, D-2Nal, or a D-isomer of another basic and/or aromatic α-amino acid; $R_{33}$ is Lys, Orn or Cys; $R_{34}$ is Aib or Asn; $R_{39}$ is Glu or Asp; and $R_{41}$ is Ala or Ile; and wherein D-Pro can be substituted for $Pro^4$ or $Pro^5$; provided however that a second cyclizing bond may exist between $R_{20}$ and $R_{23}$. When it is desired that the peptide very closely resemble r/hCRF, all or a majority of the following selections are incorporated: $R_{18}$ is Val, $R_{22}$ is Ala, $R_{23}$ is Arg, $R_{24}$ is Ala, $R_{25}$ is Glu, $R_{28}$ is Ala, $R_{39}$ is Glu, and $R_{41}$ is Ile.

A more preferred group of CRF agonists is based upon the sequences of r/hCRF and oCRF and because of the syntheses that have been carried out over the last decade, it has uniformly been shown that any of the residues in the corresponding position in ovine CRF can be substituted into the amino acid sequence of r/hCRF without significantly altering its biopotency. This group has the following amino acid sequence (including nontoxic salts thereof):
(cyclo 30-33)$Y_1$-$Y_2$-Pro-Pro-Ile-Ser-Leu-Asp-Leu-Thr-D-Phe-His-Leu-Leu-Arg-Glu-$R_{18}$-Leu-$R_{20}$-Nle-$R_{22}$-$R_{23}$-Ala-$R_{25}$-Gln-Leu-Ala-$R_{29}$-$R_{30}$-Ala-$R_{32}$-$R_{33}$-$R_{34}$-Arg-$R_{36}$-Leu-Nle-$R_{39}$-$R_{40}$-$R_{41}$-$NH_2$ wherein $Y_1$ is H or Ac; $Y_2$ is Glu, Glu-Glu, Gln-Glu, Ser-Glu-Glu, Ser-Gln-Glu, or des-$Y_2$; $R_{18}$ is Val or Nle; $R_{20}$ is Glu, D-Glu, Cys or His; $R_{22}$ is Ala, D-Ala or Thr; $R_{23}$ is Arg, Cys, Orn or Lys; $R_{25}$ is Asp or Glu; $R_{29}$ is Gln or Glu; $R_{30}$ is Glu or Cys; $R_{32}$ is His, D-His, D-Arg, imBzlD-His, D-Nal, D-Glu, D-Ala, D-Pal, D-Dpr (Nic), D-Dpr(isopropyl), D-Aph, D-Amp, D-Iamp, D-Har, D-Agl(Nic), D-Lys(isopropyl), D-Orn, D-Dbu, D-Dpr, D-Hly, D-Hly(Nic), D-Lys(Nic), D-Orn(Nic), D-Orn (isopropyl), D-(alkyl)Arg, D-(dialkyl)Arg or D-(dialkyl) Har; $R_{33}$ is Lys, Cys or Orn; $R_{34}$ is Asn or Aib; $R_{36}$ is Lys or Leu; $R_{39}$ is Glu or Asp; $R_{40}$ is Ile or Glu; and $R_{41}$ is Ile or Ala; and wherein D-Pro may be substituted for either $Pro^4$ or $Pro^5$; provided that when $R_{30}$ is Cys, $R_{33}$ is Cys; and when $R_{30}$ is Glu, $R_{33}$ is Orn or Lys; and provided further that D-Tyr or D-Leu or Phe may be substituted for D-Phe and that a second cyclizing bond may exist between $R_{20}$ and $R_{23}$.

Another preferred group of CRF agonists has the amino acid sequence (including nontoxic salts thereof): (cyclo 30-33)$Y_1$-Ser-$R_2$-Glu-Pro-Pro-Ile-Ser-Leu-Asp-Leu-Thr-$R_{12}$-$R_{13}$-$R_{14}$-$R_{15}$-Arg-$R_{17}$-$R_{18}$-$R_{19}$-$R_{20}$-Nle-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-Arg-$R_{36}$-$R_{37}$-Nle-$R_{39}$-$R_{40}$-$R_{41}$-$NH_2$ wherein $Y_1$ is an acylating agent having up to 7 carbon atoms, e.g. Ac, Fr, Acr and Bz, or hydrogen; $R_2$ is Glu or Gln; $R_{12}$ is D-Phe, D-Tyr, D-Cpa, D-Nal or D-Pal; $R_{13}$ is His, Tyr or Glu; $R_{14}$ is CML or Leu; $R_{15}$ is CML or Leu; $R_{17}$ is CML, Glu, Asn or Lys; $R_{18}$ is Val, Nle or Met; $R_{19}$ is CML, Leu, Ile, Ala or Aib; $R_{20}$ is Glu, D-Glu, Cys or His; $R_{22}$ is Ala, Aib, Thr, Asp or Glu; $R_{23}$ is Arg, Cys, Orn or Lys; $R_{24}$ is Ala or Aib; $R_{25}$ is Asp or Glu; $R_{26}$ is Gln, Asn or Lys; $R_{27}$ is CML or Leu; $R_{28}$ is Ala or Aib; $R_{29}$ is Gln, Aib or Glu; $R_{30}$ is Glu or Cys; $R_{31}$ is Ala or Aib; $R_{32}$ is His, Aib, Gly, Tyr, Ala, D-His or an equivalent D-isomer; $R_{33}$ is Lys, Orn or Cys; $R_{34}$ is Asn or Aib; $R_{36}$ is Lys, Orn, Arg, Har or Leu; $R_{37}$ is CML, Leu or Tyr; $R_{39}$ is Glu, Aib or Asp; $R_{40}$ is Ile, Aib, Thr, Glu, Ala, Val, Leu, Nle, Phe, Nva, Gly or Gln; and $R_{41}$ is Ala, Ile, Gly, Val, Leu, Nle, Phe, Nva or Gln; and wherein the N-terminus may be shortened optionally by elimination of a sequence of up to 3 residues; provided that when $R_{30}$ is Glu, $R_{33}$ is Lys or Orn and when $R_{30}$ is Cys, $R_{33}$ is Cys, and provided further that a second cyclizing bond may exist between $R_{20}$ and $R_{23}$.

Still another preferred group of CRF agonists has the amino acid sequence (including nontoxic salts thereof):
(cyclo 30-33)$Y_1$-$Y_2$-Pro-Pro-Ile-Ser-$R_8$-Asp-Leu-$R_{11}$-$R_{12}$-$R_{13}$-Leu-Leu-Arg-$R_{17}$-$R_{18}$-$R_{19}$-Glu-$R_{21}$-$R_{22}$-$R_{23}$-$R_{24}$-Glu-$R_{26}$-$R_{27}$-$R_{28}$-$R_{29}$-Glu-Ala-$R_{32}$-Lys-Asn-Arg-$R_{36}$-$R_{37}$-$R_{38}$-$R_{39}$-$R_{40}$-$R_{41}$-$NH_2$ wherein Y is Ac or hydrogen; $Y_2$ is Glu, Asp, Gly, Glu-Glu, Asn-Asp, Gln-Glu, pGlu-Gly, Ser-Glu-Glu, Asn-Asp-Asp, Ser-Gln-Glu, or des-$Y_2$; $R_8$ is Leu or Ile; $R_{11}$ is Thr or Ser; $R_{12}$ is D-Phe or D-Leu; $R_{13}$ is His or Glu; $R_{17}$ is Glu, Lys or Asn; $R_{18}$ is Val or Nle; $R_{19}$ is Leu or Ile;

$R_{21}$ is Nle or Ile; $R_{22}$ is Ala or Glu; $R_{23}$ is Arg or Lys; $R_{24}$ is Ala, Asn, Gln or Ile; $R_{26}$ is Gln, Asn or Lys; $R_{27}$ is Leu, Glu or Gln; $R_{28}$ is Ala, Arg or Lys; $R_{29}$ is Gln or Glu; $R_{32}$ is His, Gly, Ala, D-Ala, D-His or another aromatic D-isomer α-amino acid; $R_{36}$ is Lys, Arg or Leu; $R_{37}$ is Leu or Tyr; $R_{38}$ is Nle or Leu; $R_{39}$ is Glu or Asp; $R_{40}$ is Ile, Thr or Glu; and $R_{41}$ is Ala, Ile or Val; and wherein Tyr or D-Tyr may be optionally included at the N-terminus.

Yet another preferred group of CRF agonists has the amino acid sequence (including nontoxic salts thereof): (cyclo 30-33) $Y_1$-Ser-$R_2$-Glu-Pro-Pro-Ile-Ser-Leu-Asp-Leu-Thr-D-Phe-His-Leu-Leu-Arg-Glu-$R_{18}$-$R_{19}$-$R_{20}$-$R_{21}$-$R_{22}$-$R_{23}$-$R_{24}$-$R_{25}$-Gln-$R_{27}$-$R_{28}$-Gln-$R_{30}$-$R_{31}$-Hi s-$R_{33}$-$R_{34}$-Arg-Lys-Leu-Nle-$R_{39}$-Ile-$R_{41}$-NH$_2$ wherein $Y_1$ is Ac or H; $R_2$ is Glu or Gln; $R_{18}$ is Val or Nle; $R_{19}$ is CML, Leu, Ile, Ala or Aib; $R_{20}$ is Glu, D-Glu, Cys or His; $R_{21}$ is Nle or Met; $R_{22}$ is Ala, Aib or Thr; $R_{23}$ is Arg, Cys, Orn or Lys; $R_{24}$ is Ala or Aib; $R_{25}$ is Asp or Glu; $R_{27}$ is Leu or CML; $R_{28}$ is Ala or Aib; $R_{30}$ is Glu or Cys; $R_{31}$ is Ala or Aib; $R_{33}$ is Lys, Orn or Cys; $R_{34}$ is Aib or Asn; $R_{39}$ is Glu or Asp; and $R_{41}$ is Ala or Ile; and wherein the N-terminus may be shortened optionally by elimination of a sequence of up to 3 residues; provided however that a second cyclizing bond may exist between $R_{20}$ and $R_{23}$.

One more preferred group of CRF agonists has the amino acid sequence (including nontoxic salts thereof): (cyclo 30-33) $Y_1$-Ser-$R_2$-Glu-Pro-Pro-Ile-Ser-Leu-Asp-Leu-Thr-D-Phe-$R_{13}$-Leu-Leu-Arg-$R_{17}$-$R_{18}$-Leu-$R_{20}$-Nle-$R_{22}$-$R_{23}$-$_{24}$-$R_{25}$-$R_{26}$-Leu-$R_{28}$-$R_{29}$-$R_{30}$-$R_{31}$-$R_{32}$-$R_{33}$-$R_{34}$-Arg-$R_{36}$-$R_{37}$-Nle-$R_{39}$-$R_{40}$-$R_{41}$-NH$_2$ wherein $Y_1$ is Ac or hydrogen; $R_2$ is Glu or Gln; $R_{13}$ is His, Tyr or Glu; $R_{17}$ is Glu or CML; $R_{18}$ is Val, Nle or Met; $R_{20}$ is His, Cys or Glu; $R_{22}$ is Ala, Aib, Thr, Asp or Glu; $R_{23}$ is Arg, Cys, Orn or Lys; $R_{24}$ is Ala or Aib; $R_{25}$ is Asp or Glu; $R_{26}$ is Gln, Asn or Lys; $R_{28}$ is Ala or Aib; $R_{29}$ is Gln, Aib or Glu; $R_{30}$ is Glu or Cys; $R_{31}$ is Ala or Aib; $R_{32}$ is His, Aib, Gly, Tyr, Ala, D-His or an equivalent D-isomer; $R_{33}$ is Lys, Orn or Cys; $R_{34}$ is Asn or Aib; $R_{36}$ is Lys, Orn, Arg, Har or Leu; $R_{37}$ is CML, Leu or Tyr; $R_{39}$ is Glu, Aib or Asp; $R_{40}$ is Ile, Aib, Thr, Glu, Ala, Val, Leu, Nle, Phe, Nva, Gly or Gln; and $R_{41}$ is Ala, Ile, Gly, Val, Leu, Nle, Phe, Nva or Gln; and wherein the N-terminus may be shortened optionally by elimination of a sequence of up to 3 residues; provided that when $R_{30}$ is Glu, $R_{33}$ is Lys or Orn and when $R_{30}$ is Cys, $R_{33}$ is Cys; and provided further that a second cyclizing bond may exist between $R_{20}$ and $R_{23}$.

Still one more preferred group of CRF agonists has the amino acid sequence (including nontoxic salts thereof): (cyclo 30-33)$Y_1$-Ser-$R_2$-Glu-Pro-Pro-Ile-Ser-Leu-Asp-Leu-Thr-D-Phe-His-Leu-Leu-Arg-Glu-Val-Leu-Glu-Nle- Ala-$R_{23}$-Ala-Glu-Gln-Leu-Ala-Gln-$R_{30}$-Ala-His-$R_{33}$-Asn-Arg-Lys-Leu-Nle-Glu-Ile-Ile-NH$_2$ wherein $R_2$ is Glu or Gln, $R_{23}$ is Arg or Lys; $R_{30}$ is Cys or Glu; $R_{33}$ is Cys, Lys or Orn; and wherein the N-terminus may be shortened optionally by elimination of a sequence of up to 3 residues; provided that when $R_{30}$ is Cys, $R_{33}$ is Cys and when $R_{30}$ is Glu, $R_{33}$ is Lys or Orn.

Yet one more preferred group of CRF agonists has the amino acid sequence (including nontoxic salts thereof): (cyclo 30-33)$Y_1$-$Y_2$-Pro-Pro-Ile-Ser-Leu-Asp-Leu-Thr-D-Phe-$R_{13}$-Leu-Leu-Arg-$R_{17}$-$R_{18}$-$R_{19}$-Glu-Nle-$R_{22}$-$R_{23}$-Ala-$R_{25}$-Gln-$R_{27}$-Ala-$R_{29}$-Glu-Ala-$R_{32}$-$R_{33}$-$R_{34}$-Arg-$R_{36}$-$R_{37}$-Nle-$R_{39}$-$R_{40}$-$R_{41}$-NH$_2$ wherein $Y_1$ is H or an acylating agent having up to 7 carbon atoms; $Y_2$ is Ser-Glu-Glu or Ser-Gln-Glu; $R_{13}$ is His or Tyr; $R_{17}$ is Glu or CML; $R_{18}$ is Val, Nle or Met; $R_{19}$ is Leu or Aib; $R_{22}$ is Ala or Thr; $R_{23}$ is Arg or Lys; $R_{25}$ is Asp or Glu; $R_{27}$ is Leu or Glu; $R_{29}$ is Gln, Aib or Glu; $R_{32}$ is His, Ala, D-His or an equivalent D-isomer α-amino acid; $R_{33}$ is Lys or Orn; $R_{34}$ is Asn or Aib; $R_{36}$ is Lys or Leu; $R_{37}$ is CML or Leu; $R_{39}$ is Glu or Asp; $R_{40}$ is Ile or Glu; and $R_{41}$ is Ala or Ile; wherein Tyr or D-Tyr may be optionally included at the N-terminus which may be shortened by deletion of a sequence of up to 3 residues; and wherein D-Phe may be substituted by Phe, D-Tyr, D-Cpa, D-Nal or D-Pal.

Another preferred group of CRF agonists has the amino acid sequence (including nontoxic salts thereof): (cyclo 30-33)$Y_1$-$Y_2$-Pro-Pro-Ile-Ser-Leu-Asp-Leu-Thr-D-Phe-His-Leu-Leu-Arg-Glu-Val-Leu-Glu-Nle-Ala-$R_{23}$-Ala-Glu-Gln-Leu-Ala-Gln-$R_{30}$-Ala-His-$R_{33}$-Asn-Arg-Lys-Leu-Nle-Glu-Ile-Ile-NH$_2$ wherein $Y_1$ is H or Ac; $Y_2$ is Glu, Glu-Glu, Gln-Glu, Ser-Glu-Glu, Ser-Gln-Glu, or des-$Y_2$; $R_{23}$ is Arg or Lys; $R_{30}$ is Cys or Glu; $R_{33}$ is Cys, Lys or Orn; wherein D-Pro may be substituted for Pro$^4$ or Pro$^5$ and Tyr or D-Tyr may be added at the N-terminus; and wherein His$^{32}$ may optionally be, and preferably is, substituted by D-His, D-Arg, D-Tyr, D-Nal, D-Pal, D-Asn, D-Lys, D-Dpr(Nic), D-Dpr(isopropyl), D-Aph, D-Amp, D-Iamp, D-Har, D-Phe, D-Cpa, D-Agl(Nic), D-Lys(isopropyl), imBzlD-His, D-Orn, D-Dbu, D-Dpr, D-Hly, D-Hly(Nic), D-Orn(Nic), D-Orn (isopropyl), D-(lower alkyl)Arg, D-Lys(Nic), D-(lower alkyl)Amp, D-(lower dialkyl)Arg or D-(lower alkyl)Har; provided that when $R_{30}$ is Cys, $R_{33}$ is Cys and when $R_{30}$ is Glu, $R_{33}$ is Lys or Orn; and that a second cyclizing bond may exist between Glu$^{20}$ and $R_{23}$. Specific analogs of this group which are considered to be particularly biopotent from the.standpoint.of reducing blood pressure are:

cyclo(30-33)[D-Phe$^{12}$, Nle$^{21,38}$, Glu$^{30}$, Lys$^{33}$]r/hCRF;

cyclo(30-33)[D-Phe$^{12}$, Nle$^{21,38}$, Glu$^{30}$, Orn$^{33}$]r/hCRF;

cyclo(30-33)[D-Tyr$^o$, D-Phe$^{12}$, Nle$^{21,38}$, Glu$^{30}$, Lys$^{33}$]r/hCRF;

cyclo(30-33)[D-Phe$^{12}$, Nle$^{21,38}$, Glu$^{30}$, D-His$^{32}$, Lys$^{33}$]r/hCRF;

cyclo(30-33)[D-Phe$^{12}$, Nle$^{21,38}$, Glu$^{30}$, D-2Nal$^{32}$, Orn$^{33}$]r/hCRF; and cyclo(30-33)[D-Phe$^{12}$, Nle$^{21,38}$, Glu$^{30}$, D-Iamp$^{32}$, Lys$^{33}$]r/hCRF.

Yet another preferred group of CRF agonists has the amino acid sequence (including nontoxic salts thereof): (cyclo 30-33)$Y_1$-$Y_2$-Pro-Pro-Ile-Ser-Leu-Asp-Leu-Thr-D-Phe-His-$R_{14}$-$R_{15}$-Arg-$R_{17}$-Val-$R_{19}$-Glu-Nle-Ala-$R_{23}$-Ala-Glu-Gln-$R_{27}$-Ala-Gln-$R_{30}$-Ala-$R_{32}$-$R_{33}$-Asn-Arg-Lys-$R_{37}$-Nle-Glu-Ile-Ile-NH$_2$ wherein $Y_1$ is H or Ac; $Y_2$ is Glu, Glu-Glu, Gln-Glu, Ser-Glu-Glu, Ser-Gln-Glu, or des-$Y_2$; $R_{14}$, $R_{15}$, $R_{19}$ $R_{27}$ and $R_{37}$ are independently Leu or CML; $R_{17}$ is Glu or CML; $R_{23}$ is Arg or Lys; $R_{30}$ is Glu or Cys; $R_{32}$ is D-His, D-Amp, D-Iamp, D-Arg, D-Asn, D-Tyr, D-Pal, D-Nal or another basic and/or aromatic D-isomer α-amino acid; $R_{33}$ is Lys, Orn or Cys; wherein D-Pro may be substituted for Pro$^4$ or Pro$^5$, and wherein at least one of $R_{14}$, $R_{15}$, $R_{17}$, $R_{19}$, $R_{27}$and $R_{37}$ is CML; provided that when $R_{30}$ is Cys, $R_{33}$ is Cys and when $R_{30}$ is Glu, $R_{33}$ is Lys or Orn. Specific analogs of this group which are considered to be particularly biopotent from the standpoint of reducing blood pressure are:

cyclo(30-33)[Ac-D-Pro$^4$, D-Phe$^{12}$, Nle$^{21,38}$, CML$^{27}$, Glu$^{30}$, D-His$^{32}$, Lys$^{33}$]r/hCRF(4-41);

cyclo(30-33)[D-Pro$^5$, D-Phe$^{12}$, CML$^{15}$, Nle$^{21,38}$, Glu$^{30}$, D-Pal$^{32}$, Lys$^{33}$]r/hCRF(4-41);

cyclo(30-33)[Ac-Pro$^4$, D-Phe$^{12}$, CML$^{15}$, Nle$^{21,38}$, Glu$^{30}$, D-His$^{32}$, Lys$^{33}$]r/hCRF(4-41);

cyclo(30-33)[D-Phe$^{12}$, CML$_{14}$, Nle$^{21,38}$, Glu$^{30}$, D-His$^{32}$, Lys$^{33}$] r/hCRF(4-41);

cyclo(30-33)[Ac-D-Pro$^4$, D-Phe$^{12}$, Nle$^{21,38}$, Glu$^{30}$, D-His$^{32}$, Lys$^{33}$, CML$^{37}$]r/hCRF(4-41);

cyclo(30-33)[D-Phe$^{12}$, CML$^{17}$, Nle$^{21,38}$, Glu$^{30}$, D-His$^{32}$, Lys$^{33}$] r/hCRF(4-41); and cyclo(30-33)[D-Pro$^5$, D-Phe$^{12}$, CML$^{19}$, Nle$^{21,38}$, Glu$^{30}$, D-His$^{32}$, Lys$^{33}$]r/hCRF(4-41).

A particularly preferred group of CRF agonists has the amino acid sequence (including nontoxic salts thereof): (cyclo 30-33)Y$_1$-Y$_2$-Pro-Pro-Ile-Ser-Leu-Asp-Leu-Thr-D-Phe-His-Leu-Leu-Arg-Glu-Val-Leu-Glu-Nle-Ala-R$_{23}$-Ala-Glu-Gln-Leu-Ala-Gln-R$_{30}$-Ala-His-R$_{33}$-Asn-Arg-Lys-Leu-Nle-Glu-Ile-Ile-NH$_2$ wherein Y$_1$ is H or Ac; Y$_2$ is Glu, Glu-Glu, Gln-Glu, Ser-Glu-Glu, Ser-Gln-Glu, or des-Y$_2$; R$_{23}$ is Arg or Lys; R$_{30}$ is Cys or Glu; R$_{33}$ is Cys, Lys or Orn; wherein Tyr or D-Tyr may be optionally included at the N-terminus, wherein D-Phe may be substituted by Phe, wherein D-Pro may be substituted for Pro$^4$ or Pro$^5$, and wherein His$^{32}$ may optionally be, and preferably is, substituted by D-His, D-Amp, D-Iamp, D-Arg, D-Pal, D-Nal or a D-isomer of another natural amino acid other than Cys; provided that when R$_{30}$ is Cys, R$_{33}$ is Cys and when R$_{30}$ is Glu, R$_{33}$ is Lys or Orn. Specific analogs of this group which are considered to be particularly biopotent from the standpoint of reducing blood pressure are:

cyclo(30-33)[Ac-Pro$^4$, D-Phe$^{12}$, Nle$^{21,38}$, Glu$^{30}$, D-His$^{32}$, Lys$^{33}$]r/hCRF(4-41);

cyclo(30-33)[Ac-Pro$^4$, D-Phe$^{12}$, Nle$^{21,38}$, Glu$^{30}$, D-His$^{32}$, Orn$^{33}$]r/hCRF(4-41);

cyclo(30-33)[Ac-Pro$^4$, D-Phe$^{12}$, Nle$^{21,38}$, Cys$^{30,33}$, D-His$^{32}$]r/hCRF(4-41);

cyclo(30-33)[Ac-D-Pro$^4$, D-Phe$^{12}$, Nle$^{21,38}$, Glu$^{30}$, D-2Nal$^{32}$, Lys$^{33}$]r/hCRF(4-41);

cyclo(30-33)[Tyr$^o$, D-Phe$^{12}$, Nle$^{21,38}$, Glu$^{30}$, D-His$^{32}$, Lys$^{33}$] r/hCRF; and cyclo(30-33)[Pro$^5$, D-Phe$^{12}$, Nle$^{21,38}$, Glu$^{30}$, D-3Pal$^{32}$, Lys$^{33}$] r/hCRF.

When Tyr or D-Tyr is added to the extended N-terminus, the peptide can be conveniently radiolabelled using $^{125}$I.

The peptides are synthesized by a suitable method, such as by exclusively solid-phase techniques, by partial solid-phase techniques, by fragment condensation or by classical solution addition.

Common to chemical syntheses of peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

For example, chemical synthesis of a peptide analog from one preferred group may include the initial formation of an intermediate of the following amino acid sequence:
X$^1$-R$_1$(X$^2$ or X$^4$)-R$_2$(X$^4$ or X$^5$)-R$_3$(X$^5$)-Pro-Pro-R$_6$-Ser(X$^2$)-R$_8$-Asp(X$^5$)-Leu-R$_{11}$(X$^2$)-D-Phe-R$_{13}$(X$^7$ or X$^5$)-Leu-Leu-Arg(X$^3$)-R$_{17}$(X$^5$)-R$_{18}$-Leu-R$_{20}$(X$^5$ or X$^8$)-Nle-R$_{22}$(X$^2$ or X$^5$)-R$_{23}$(X$^3$, X$^6$ or X$^8$)-R$_{24}$- R$_{25}$(X$^5$)-R$_{26}$(X$^4$ or X$^6$)-Leu-R$_{28}$-R$_{29}$(X$^4$ or X$^5$)-R$_{30}$(X$^5$ or X$^8$)-R$_{31}$-R$_{32}$(X$^3$ or X$^7$)-R$_{33}$ (X$^6$ or X$^8$)-R$_{34}$(X$^4$)-Arg(X$^3$)-R$_{36}$(X$^3$ or X$^6$)-R$_{37}$(X$^7$)-Nle-R$_{39}$(X$^5$)-R$_{40}$(X$^2$, X$^4$ or X$^5$)-R$_{41}$(X$^4$)-X$^9$ wherein: the R-groups are as hereinbefore defined.

X$^1$ is either hydrogen or an alpha-amino protecting group. The alpha-amino protecting groups contemplated by X$^1$ are those known to be useful in the art in the step-wise synthesis of polypeptides. Among the classes of alpha-amino protecting groups covered by X$^1$ are (1) acyl-type protecting groups, such as formyl(Fr), acrylyl(Acr), benzoyl(Bz) and acetyl(Ac) which are preferably used only at the N-terminal; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as fluorenyl methyloxycarbonyl (Fmoc), cyclopentyloxy-carbonyl, adamantyloxycarbonyl, and cyclohexyloxy-carbonyl; and (5) thiourethan-type protecting groups, such as phenylthiocarbonyl. The two preferred alpha-amino protecting groups are BOC and Fmoc.

X$^2$ is a protecting group for the hydroxyl group of Thr and Ser and is preferably selected from the class consisting of acetyl(Ac), benzoyl(Bz), tert-butyl, triphenylmethyl(trityl), tetrahydropyranyl, benzyl ether(Bzl) and 2,6-dichlorobenzyl (DCB). The most preferred protecting group is Bzl. X$^2$ can be hydrogen, which means there is no protecting group on the hydroxyl group.

X$^3$ is a protecting group for the guanidino group of Arg or Har preferably selected from the class consisting of nitro, p-toluenesulfonyl(Tos), Z, adamantyloxycarbonyl and BOC, or is hydrogen. Tos is most preferred.

X$^4$ is hydrogen or a protecting group, preferably xanthyl (Xan), for the amido group of Asn or Gln. Asn or Gln is often coupled without side chain protection in the presence of hydroxybenzotriazole (HOBt).

X$^5$ is hydrogen or an ester-forming protecting group for the β- or γ-carboxyl group of Asp or Glu, preferably selected from the esters of cyclohexyl (OChx) benzyl (OBzl), 2,6-dichlorobenzyl, methyl, ethyl and t-butyl (Ot-Bu). OChx is preferred for a BOC strategy.

X$^6$ is hydrogen or a protecting group for the side chain amino substituent of Lys or Orn. Illustrative of suitable side chain amino-protecting groups are Z, 2-chlorobenzyloxycarbonyl(2Cl-Z), Tos, t-amyloxycarbonyl(Aoc), BOC and aromatic or aliphatic urethan-type protecting groups as specified hereinbefore. 2Cl-Z is preferred for a BOC strategy.

When His is present, X$^7$ is hydrogen or a protecting group for the imidazole nitrogen such as Tos or 2,4-dinitrophenyl (DNP), and when Tyr is present, X$^7$ is hydrogen or a protecting group for the hydroxyl group such as DCB. When Met is present, the sulfur may be protected, if desired, with oxygen.

X$^8$ is a protecting group for the sulfhydryl group of Cys, preferably p-methoxybenzyl(MeOBzl), p-methylbenzyl, acetamidomethyl, trityl or Bzl; or a suitable protecting group for an amino side chain which is removable without simultaneously removing the protecting group X$^6$, e.g. a base-labile group such as Fmoc; or a suitable labile protecting group for a carboxyl side chain which is removable without simultaneously removing the protecting group X$^5$, e.g., a base-labile group such as OFm (fluorenylmethyl ester). Alternatively it may be a direct bond between the residues in the 30- and 33-positions, or the residues in the 20- and 23-positions, e.g. when the cyclic form results from a carba or dicarba bond which is considered to be equivalent to a Cys-Cys bond.

The selection of a side chain amino protecting group is not critical except that it should be one which is not removed during deprotection of the alpha-amino groups during the synthesis. Hence, the alpha-amino protecting group and the side chain amino protecting group cannot be the same.

$X^9$ is $NH_2$, a protecting group such as an ester or an anchoring bond used in solid phase synthesis for linking to a solid resin support, preferably one represented by the amino acid sequence: —NH-benzhydrylamine (BHA) resin support and —NH-paramethylbenzhydrylamine (MBHA) resin support. Cleavage from a BHA or MBHA resin directly gives the CRF analog amide. By employing a methyl-derivative of such a resin, a methyl-substituted amide can be created, which is considered to be the equivalent thereof.

In the amino acid sequence for the intermediate, at least one of $X^1$, $X^2$, $X^3$, $X^4$, $X^5$, $X^6$, $X^7$ and $X^8$ is a protecting group or $X^9$ includes resin support. The particular amino acid chosen for each R-group determines whether there will also be a protecting group attached as specified hereinbefore and as generally known in the art. In selecting a particular side chain protecting group to be used in the synthesis of the peptides, the following rules are followed: (a) the protecting group should be stable to the reagent and under the reaction conditions selected for removing the alpha-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

If the N-terminus is modified, an acyl group is preferably present, as represented by $Y_1$, and acetyl (Ac), formyl(Fr), acrylyl(Acr) and benzoyl(Bz) are the preferred acyl groups with Nph and Flu being alternatives. However, $Y_1$ may alternatively be a suitable sugar or lipid, which are generally considered to be equivalents.

Thus, in one aspect, there is also provided a process for the manufacture of compounds comprising (a) forming a peptide intermediate, as defined hereinbefore, having at least one protective group wherein: $X^1$, $X^2$, $X^3$, $X^4$, $X^5$, $X^6$, $X^7$ and $X^8$ are each either hydrogen or a protective group, and $X^9$ is either a protective group or an anchoring bond to resin support or $NH_2$, (b) forming a cyclizing bond, particularly if one has not already been formed, (c) splitting off the protective group or groups or the anchoring bond from said peptide intermediate, (d) optionally forming a cyclizing bond at this time, and (e) if desired, converting a resulting peptide into a nontoxic addition salt thereof.

The peptides are preferably prepared using solid phase synthesis, such as that described by Merrifield, *J. Am. Chem. Soc.*, 85, p 2149 (1964). Thus, CRF antagonist peptides can be prepared in a straightforward manner and then simply tested for biological activity. This facilitates the ready preparation and evaluation of CRF antagonist peptides. Solid-phase synthesis is commenced from the C-terminus of the peptide by coupling a protected alpha-amino acid to a suitable resin as generally set forth in U.S. Pat. No. 4,244,946 issued Jan. 21, 1981 to Rivier et al. Such a starting material for an antagonist based upon human CRF can be prepared by attaching alpha-amino-protected Ile to an MBHA resin.

Ile protected by BOC is coupled to the BHA resin using methylene chloride and/or dimethylformamide (DMF) and/or N-methyl pyrrolidone (NMP). Following the coupling of BOC-Ile to the resin support, the alpha-amino protecting group is removed, as by using trifluoroacetic acid(TFA) in methylene chloride, TFA alone or with HCl in dioxane. Preferably 50 volume % TFA in methylene chloride is used with 0–5 weight % 1,2 ethanedithiol. The deprotection is carried out at a temperature between about 0° C. and room temperature. Other standard cleaving reagents and conditions for removal of specific alpha-amino protecting groups may be used, as described in Schroder & Lubke, "The Peptides", Vol. 1, 72–75 (Academic Press 1965) and in the well known Barany-Merrifield text.

After removal of the alpha-amino protecting group of Ile, the remaining alpha-amino- and side chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as coupling reagents are N,N'-dicyclohexyl carbodiimide(DCC) and N,N'-diisopropyl carbodiimide(DICI).

Activating or coupling reagents for use in the solid phase synthesis of the peptides are well known in the peptide art. Examples of suitable activating reagents are carbodiimides, such as N,N'-diisopropyl carbodiimide and N-ethyl-N'-(3-dimethylaminopropyl) carbodiimide. Other activating reagents and their use in peptide coupling are described by Schroder & Lubke, supra, in Chapter III and by Kapoor, *J. Phar. Sci.*, 59, pp 1–27 (1970). P-nitrophenyl ester (ONp) can also be used to activate the carboxyl end of Asn or Gln for coupling. For example, BOC-Asn(ONp) can be coupled overnight using one equivalent of HOBt in a 50% mixture of DMF and methylene chloride.

Each protected amino acid or amino acid sequence is introduced into the solid phase reactor in about a threefold excess, and the coupling is carried out in a medium of dimethylformamide(DMF):$CH_2Cl_2$ (1:1) or in $CH_2Cl_2$ alone at room temperature. Alternatively, coupling may be carried out at elevated temperature up to about 70° C. in NMP in a mixture of toluene:DMSO (70:30). In instances where the coupling is carried out manually, the success of the coupling reaction at each stage of the synthesis is monitored by the ninhydrin reaction, as described by E. Kaiser et al., *Anal. Biochem.* 34, 595 (1970). In cases where incomplete coupling occurs, the coupling procedure is repeated before removal of the alpha-amino protecting group prior to the coupling of the next amino acid. The coupling reactions can be performed automatically, as on a Beckman 990 automatic synthesizer, using a program such as that reported in Rivier et al., *Biopolymers*, 17, pp. 1927–1938, (1978).

After the desired amino acid sequence has been completed, the intermediate peptide is removed from the resin support unless it is desired to form the cyclizing bond while attached to the resin, as described hereinafter. Removal is effected by treatment with a reagent, such as liquid hydrogen fluoride (HF), which not only cleaves the peptide from the resin but also cleaves all remaining side chain protecting groups $X^2$, $X^3$, $X^4$, $X^5$, $X^6$ and $X^7$ and the alpha-amino protecting group $X^1$, if still present (unless it is an acyl group which is intended to be present in the final peptide), to obtain the peptide. When using hydrogen fluoride for cleaving, anisole or cresol and methylethyl sulfide are included in the reaction vessel as scavengers. When Met is present in the sequence, the BOC protecting group may be cleaved with trifluoroacetic acid(TFA)/ethanedithiol prior to cleaving the peptide from the resin to eliminate S-alkylation.

The cyclizing step for the CRF peptide analog depends, of course, upon the type of linkage which is desired between the residues in the 30- and 33-positions (and similarly for those in the 20- and 23-positions when a bi-cyclic molecule is being formed). When residues of L-Cys are included in both the 30- and 33-positions, it is often more convenient to carry out the cyclizing step following the cleavage from the resin and the removal of all of the protecting groups from the peptide. The cyclic form of the peptide is obtained by oxidization using a ferricyanide solution, preferably as described in Rivier et al., *Biopolymers*, Vol. 17 (1978), 1927–38, or by air oxidation, or in accordance with other known procedures.

To effect an amide cyclizing linkage (lactam bridge), cyclization may be carried out while the partially protected peptide remains attached to the resin as disclosed in U.S. Pat. Nos. 5,064,939 and 5,043,322. Such a procedure effectively creates an amide cyclizing bond between the two desired side chains while other residues, such as Asp, Glu and/or Lys, in the peptide intermediate retain their side-chain protection.

When cyclizing via an amide bond between a side-chain carboxyl group of the 30-position residue and a side-chain amino group of the 33-position residue, or vice-versa which is generally considered to be an equivalent linkage, it is preferable to synthesize the protected peptide on an MBHA or BHA resin and to derivatize the benzyl ester of the particular carboxyl acid side chain to the hydrazide while the peptide is still attached to the resin and then react it with a selectively deprotected amino-side chain as set forth in U.S. Pat. No. 5,043,322. Preferably cyclization is accomplished by using a base-labile protecting group, e.g., OFm, for the carboxyl side-chain of the residue to be involved in the amide-bond bridge and using Fmoc as a protecting group for the amino side chain on the other residue that is to be involved. The α-amino protecting group on the 1-position residue, whether or not it is to be acylated, and all of the other side-chain protecting groups remain in place while the two base-labile groups are removed using piperidine or the like. Following this selective removal, the reaction to accomplish cyclization is carried out by treating with BOP which effects substantially complete generation of the amide bond. If 2 lactam bridges are to be incorporated in the molecule, the 30-33 bridge is preferably effected at a point in the synthesis prior to adding the 23-position residue, or a synthesis protocol such as taught in U.S. Pat. No. 5,064,939 is employed. Following cyclization, the peptide is completely deprotected and cleaved from the resin using a reagent, such as HF. Optionally, a BOC-protecting group can be first removed from the N-terminus using TFA.

Alternatively, cyclizations of peptides by such amide linkages can also be effected using teachings of U.S. Pat. Nos. 4,115,554, (Sep. 19, 1978); 4,133,805 (Jan. 9, 1979); 4,140,767 (Feb. 20, 1979); 4,161,521 (Jul. 17, 1979); 4,191,754 (Mar. 4, 1980); 4,238,481 (Dec. 9, 1980); 4,244,947 (Jan. 13, 1981); and 4,261,885 (Apr. 14, 1981).

A straightforward assay can be carried out using rat anterior pituitary cells in monolayer culture to determine what CRF-activity a candidate peptide will exhibit; the procedure which is used is that generally set forth in *Endocrinology*, 91, 562 (1972). The assay is employed to show whether a candidate peptide will exhibit some activity as a CRF agonist by stimulating ACTH secretion by activating CRF receptors on such cells, and its antagonistic properties are determined by comparison to the results obtained from a parallel dose of oCRF which is used as a laboratory "standard" for this purpose.

A candidate CRF agonist peptide is also easily evaluated in a binding assay using a known CRF receptor, such as that described in Perrin, M., et al., *Endocrinology*, 118, 1171–1179 (1986). A representative binding assay utilizing CRF-RA receptor is described in Chen, et al., *P.N.A.S.*, 90, 8967–8971 (October 1993). These cyclic peptides having a D-amino acid residue in position 32 exhibit high binding affinity to CRF receptors, such as CRF-RA. As such, they may be used to screen for potential CRF agonists with even higher affinity by using a labelled cyclic CRF agonist.

As hereinbefore indicated, a cyclizing bond between the residues in the 30- and 33-positions and the substitution of a D-isomer amino acid in the 32-position enhances the properties of agonists throughout the CRF family of peptides. These agonists, as well known in the art, can include the entire 41-residue peptide or can be slightly shortened at the N-terminus by deleting a sequence of 3 residues or as many as 5 residues, if desired. The N-terminus of these CRF agonists can be acylated by an acylating agent as known in the art generally having up to 15 carbon atoms, and preferably from 1 to 7 carbon atoms, such as acetyl, acrylyl and benzoyl. The following examples set forth preferred methods for synthesizing CRF agonists by the solid-phase technique.

EXAMPLE 1

The synthesis of (cyclo 30-33)[Ac-Pro$^4$, D-Phe$^{12}$, Nle$^{21,38}$, Glu$^{30}$, D-His$^{32}$, Lys$^{33}$]-r/hCRF(4-41) having the amino acid sequence: Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu-Ala- Gln-Glu-Ala-D-His-Lys-Asn-Arg-Lys-Leu-Nle-Glu-Ile-Ile-NH$_2$ is conducted in a stepwise manner on a MBHA hydrochloride resin, such as available from Bachem, Inc., having a substitution range of about 0.1 to 0.5 mmoles/gm. resin. The synthesis is performed on an automatic Beckman 990B peptide synthesizer using a suitable program, preferably as follows:

| STEP | REAGENTS AND OPERATIONS | MIX TIMES MIN. |
|---|---|---|
| 1 | CH$_2$Cl$_2$ wash-80 ml. (2 times) | 1 |
| 2 | Methanol(MeOH) wash-30 ml. (2 times) | 1 |
| 3 | CH$_2$Cl$_2$ wash-80 ml. (3 times) | 1 |
| 4 | 50 percent TFA plus 5 percent 1,2-ethane-dithiol in CH$_2$Cl$_2$-70 ml. (2 times) | 12 |
| 5 | Isopropanol wash-80 ml. (2 times) | 1 |
| 6 | TEA 12.5 percent in CH$_2$Cl$_2$-70 ml. (2 times) | 1 |
| 7 | MeOH wash-40 ml. (2 times) | 1 |
| 8 | CH$_2$Cl$_2$ wash-80 ml. (3 times) | 1 |
| 9 | BOC-amino acid (10 mmoles) in 30 ml. of either DMF or CH$_2$Cl$_2$, depending upon the solubility of the particular protected amino acid, (1 time) plus DCC (10 mmoles) in CH$_2$Cl$_2$ | 30–300 |

Coupling of BOC-Ile results in the substitution of about 0.35 mmol. Ile per gram of resin. All solvents that are used are carefully degassed, preferably by sparging with an inert gas, e.g., helium or nitrogen.

After deprotection and neutralization, the peptide chain is built step-by-step on the resin. Generally, one to two mmol. of BOC-protected amino acid in methylene chloride is used per gram of resin, plus one equivalent of 2 molar DCC in methylene chloride, for two hours. When BOC-Arg(Tos) is being coupled, a mixture of 50% DMF and methylene chloride is used. Bzl is used as the hydroxyl side-chain protecting group for Ser and Thr. P-nitrophenyl ester(ONp) can be used to activate the carboxyl end of Asn or Gln; for example, BOC-Asn(ONp) can be coupled overnight using one equivalent of HOBt in a 50% mixture of DMF and methylene chloride. The amido group of Asn or Gln is protected by Xan when DCC coupling is used instead of the active ester method. 2-Cl-Z is used as the protecting group for the Lys side chain unless the Lys residue is to take part in the lactam bridge when Fmoc is used. Tos is used to protect the guanidino group of Arg and the imidazole group of His, and the side-chain carboxyl group of Glu or Asp is protected by OBzl except for $Glu^{30}$ which is protected by OFm. At the end of the synthesis, the following composition is obtained:

BOC-Pro-Pro-Ile-Ser(Bzl)-Leu-Asp(OBzl)-Leu-Thr(Bzl)-D-Phe-His(Tos)-Leu-Leu-Arg(Tos)-Glu(OBzl)-Val-Leu-Glu (OBzl)-Nle-Ala-Arg(Tos)-Ala-Glu(OBzl)-Gln(Xan)-Leu-Ala-Gln(Xan)-Glu(OFm)-Ala-D-His(Tos)-Lys(Fmoc)-Asn (Xan)-Arg(Tos)-Lys(2Cl-Z)-Leu-Nle-Glu(OBzl)-Ile-Ile-resin support. Xan may have been partially or totally removed by TFA treatment used to deblock the alpha-amino protecting group.

Next cyclization (lactamization) of residues 30 and 33 is performed by the method referred to hereinbefore and described more fully as follows. After washes with dichloromethane (DCM) (2×) and dimethylformamide (DMF) (2×), the OFm/Fmoc groups of $Glu^{30}$ and $Lys^{33}$, respectively, are removed by 20% piperidine in DMF (1×1 min. and 2×10 min.), followed by washing with DMF (2×), $ET_3N$ in $CH_2Cl_2$ (1×), methanol (MeOH) (2×) and DCM (2×). The peptide-resin is cyclized by reaction at room temperature with threefold excess of benzotriazol-1-yl-oxy-tris(dimethylamino)phosphonium hexafluorophosphate (BOP) in presence of excess diisoproplyethylamine (DIEA) in dimethylformamide (DMF). After washing, the cyclization is repeated two more times for four hours and then once for twelve hours if necessary. The completion of the reaction is confirmed by the well known Kaiser ninhydrin test. In general, it is complete in no more than 24 hours.

Following cyclization, the peptide-resin is treated with TFA to remove the BOC protecting group at the N-terminus. It is then reacted with acetic anhydride to acetylate the proline residue. The resulting peptide-resin is cleaved and deprotected by treatment with 1.5 ml. anisole, 0.5 ml. of methylethylsulfide and 15 ml. hydrogen fluoride (HF) per gram of peptide-resin, first at −20° C. for 20 min. and then at 0° C. for one-half hour. After elimination of the HF under high vacuum, the. resin-peptide is washed alternately with dry diethyl ether and chloroform, and the peptide is then extracted with de-gassed 2N aqueous acetic acid and separated from the resin by filtration.

The peptide is purified by gel permeation followed by preparative HPLC as described in Marki, et al.,*J. Am. Chem. Soc.*, 103, 3178 (1981); Rivier, et al., *J. Chromatography*, 288, 303–328 (1984); and Hoeger, et al., *BioChromatography*, 2, 3, 134–142 (1987). The chromatographic fractions are carefully monitored by HPLC, and only the fractions showing substantial purity are pooled.

To check whether the precise sequence is achieved, the r/hCRF analog is hydrolyzed in sealed evacuated tubes containing constant boiling HCl, 3 μl of thioglycol/ml. and 1 nmol of Nle (as an internal standard) for 9 hours at 140° C. Amino acid analysis of the hydrolysates using a Beckman 121 MB amino acid analyzer shows amino acid ratios which confirm that the 38-residue peptide structure has been obtained.

The peptide is judged to be homogeneous using reversed-phase high performance liquid chromatography (RP-HPLC). It is specifically subjected to RP-HPLC using a Waters HPLC system with a 0.46×25 cm. column packed with 5 μm $C_{18}$ silica, 300 Å pore size and TEAP buffers at different pHs. Desalting of the purified peptide is achieved using Buffer A which is an aqueous 0.1% trifluoroacetic acid solution consisting of 1.0 ml. of TFA per 1000 ml. of solution and Buffer B which is 100% acetonitrile. It has a purity of greater than 90% measured by capillary zone electrophoresis (CZE). Liquid secondary ion mass spectrometry (LSIMS) mass spectra are measured with a JEOL model JMS-HX110 double-focusing mass spectrometer fitted with a $Cs^{30}$ gun. An accelerating voltage of 10 kV and $Cs^{30}$ gun voltage between 25 and 30 kV are employed. The measured value of 4440.49 obtained using LSIMS is in agreement with the calculated value of 4440.52.

Specific optical rotation of the h/rCRF peptide, that was synthesized and purified in the foregoing manner, is measured on a Perkin Elmer Model 241 Polarimeter as $[\alpha]_D^{22}$= −33.2°±1 (c=1 in 10% acetic acid without correction for the presence of $H_2O$ and TFA).

The synthesis is repeated twice. Once, the cyclic peptide with His instead of D-His in the 32-position is produced, and then by omitting the cyclization step, the comparable linear peptide with $His^{32}$ is produced. The optical rotations of the $His^{32}$ peptides are measured as before as $[\alpha]_D^{22}$=−38.9°±1 (cyclic) and $[\alpha]_D^{22}$=−39.5°±1(linear) with the cyclic peptide being measured in 9% acetic acid and the linear peptide in 1% acetic acid.

The cyclic CRF agonist with $D-His^{32}$ is examined for its effects on the secretion of ACTH and β-endorphin in vitro and also in vivo. Its in vitro potency to stimulate the secretion of ACTH and β-endorphin by cultured rat pituitary cells is measured using the procedure generally set forth in *Endocrinology*, 91, 562 (1972) and compared against synthetic oCRF. It is found to be about 201 times (102–420) as potent as the native hormone. In vitro testing of the cyclic $His^{32}$ peptide shows a potency of 6.3 times (3.2–12.9) that of the standard oCRF, whereas the linear peptide is about 4.5 times (2.7–7.6) as potent as the native hormone.

It can be seen that the $D-His^{32}$ substitution very significantly further increases biopotency of the cyclic CRF agonist peptide. In vivo testing is carried out using the general procedure set forth in C. Rivier et al., *Science*, 218, 377 (1982) and shows a significant lowering of blood pressure when this peptide is administered peripherally.

EXAMPLE 1A

The synthesis of Example 1 for the cyclic $D-His^{32}$ peptide is repeated using a triple batch and extending the N-terminus instead of terminating the amino acid chain at Pro. Three additional residues are sequentially added, i.e. Glu, Glu and then Ser, each time removing ⅓ of the original amount of resin. Following cyclization, the N-termini of the CRF(3-41) and the CRF(2-41) peptides are acetylated. The following three peptides are produced:

(cyclo 30-33)[Ac-$Glu^3$, D-$Tyr^{12}$, $Nle^{21,38}$, $Glu^{30}$, D-$His^{32}$, $Lys^{33}$]-r/hCRF(3-41);

(cyclo 30-33)[(Ac-$Glu^2$, D-$Tyr^{12}$, $Nle^{21,38}$, $Glu^{30}$, D-$His^{32}$, $Lys^{33}$]-r/hCRF(2-41); and (cyclo 30-33)[D-$Tyrl^{12}$, $Nle^{21,38}$, $Glu^{30}$, D-$His^{32}$, $Lys^{33}$] -r/hCRF.

Each peptide has a purity of about 98% as confirmed by capillary zone electrophoresis (CZE). The biopotency of each peptide is measured in vitro, as previously described, and compared to the laboratory Standard, i.e. ovine CRF. Each is substantially more potent than the Standard by about the same amount as the cyclic D-$Phe^{32}$ peptide of Example 1.

EXAMPLE 1B

The synthesis of Example 1 is again repeated, this time adding H-Tyr-Ser-Glu-Glu to Pro at the N-terminus to produce the following peptide:

(cyclo 30-33)[Tyr$^o$, D-Phe$^{12}$, Nle$^{21,38}$, Glu$^{30}$, D-His$^{32}$, Lys$^{33}$]-r/hCRF. The peptide's biopotency, in vitro, is very substantially greater than that of the laboratory Standard. The peptide is readily radioiodinated with $^{125}$I to provide a ligand for use in competitive drug screening assays.

EXAMPLE 2

The peptide (cyclo 30-33)[D-Phe$^{12}$, Nle$^{21,38}$, Glu$^{30}$, D-His$^{32}$, Orn$^{33}$]-rCRF(3-41) having the amino acid sequence: H-Glu-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu- Ala-Gln-Glu-Ala-D-His-Orn-Asn-Arg-Lys-Leu-Nle-Glu-Ile-Ile-NH$_2$ is synthesized using the procedure as generally set forth in Example 1. Testing in accordance with the general procedure set forth in Example 1 shows that it likewise stimulates the secretion of ACTH and β-END-LI and causes a very significant lowering of blood pressure when administered peripherally.

EXAMPLE 3

The peptide (cyclo 30-33)[Ac-Pro$^4$, D-Phe$^{12}$, Nle$^{21,38}$, Glu$^{30}$, D-His$^{32}$, Lys$^{33}$]-oCRF(4-41) having the amino acid sequence: Ac-Pro-Pro-Ile-Ser-Leu-Asp-Leu-Thr-D-Phe-His-Leu-Leu-Arg-Glu-Val-Leu-Glu-Nle-Thr-Lys-Ala- Asp-Gln-Leu-Ala-Gln-Glu-Ala-D-His-Lys-Asn-Arg-Lys-Leu-Nle-Asp-Ile-Ala-NH$_2$ is synthesized using a procedure generally as set forth in Example 1. A portion of the peptide-resin is removed prior to cyclization in order to produce the linear peptide with D-His in the 32-position. Testing in accordance with the general procedure set forth hereinbefore shows that the cyclic peptide highly stimulates the secretion of ACTH and β-END-LI and causes a very significant lowering of blood pressure when administered peripherally.

Testing also shows that the linear peptide with the D-His$^{32}$ substitution has an in vitro biopotency very substantially less than the cyclic compound.

EXAMPLE 3A

The peptide (cyclo 30-33)[Ac-Pro$^4$, D-Phe 12, Nle$^{18,21}$, Glu$^{30}$, D-Ala$^{32}$, Lys$^{33}$]-AHC(4-41) having the amino acid sequence: Ac-Pro-Pro-Ile-Ser-Leu-Asp-Leu-Thr-D-Phe-His-Leu-Leu-Arg-Glu-Nle-Leu-Glu-Nle-Ala-Lys-Ala-Glu-Gln-Glu-Ala-Glu-Glu-Ala-D-Ala-Lys-Asn-Arg-Leu-Leu-Leu-Glu-Glu-Ala-NH$_2$ is synthesized using a procedure generally as set forth in Example 1. A portion of the peptide-resin is removed prior to cyclization, and it is cleaved and deprotected to provide the corresponding linear peptide. Amino acid analysis of the two resultant, purified peptides is consistent with the amino acid sequence for the prepared peptides and confirms that the 38-residue peptide structures are obtained. The cyclic peptide has a value of 4336.63 when measured by LSIMS which is in agreement with the calculated value of 4336.36. Testing in accordance with the general procedure set forth hereinbefore shows that the cyclic peptide strongly stimulates the secretion of ACTH and β-END-LI and causes a very significant lowering of blood pressure when administered peripherally. The linear peptide has bioactivity but of a very significantly lesser degree.

The above synthesis is repeated to produce the cyclic peptide with D-His in the 32-position. Testing shows that the D-His$^{32}$ cyclic analog also exhibits significantly increased biopotency compared to the linear peptide tested above.

EXAMPLE 3B

The peptide (cyclo 30-33)[D-Phe$^{12}$, Nle$^{18,21}$, Glu$^{30}$, Lys$^{33}$]-sucker urotensin having the amino acid sequence: H-Asn-Asp-Asp-Pro-Pro-Ile-Ser-Ile-Asp-Leu-Thr-D-Phe-His-Leu-Leu-Arg-Asn-Nle-Ile-Glu-Nle-Ala-Arg-Ile-Glu-Asn-Glu- Arg-Glu-Glu-Ala-Gly-Lys-Asn-Arg-Lys-Tyr-Leu-Asp-Glu-Val-NH$_2$ is synthesized using a procedure generally as set forth in Example 1. Amino acid analysis of the resultant, purified peptide is consistent with the amino acid sequence for the prepared peptide and confirms that the 41-residue peptide structure is obtained. It has a purity of about 98% confirmed by capillary zone electrophoresis. LSIMS shows a value of 4829.78 which agrees with the calculated value of 4829.53. The peptide's biopotency, determined as previously described, is several times that of the Standard.

The synthesis is repeated twice to produce the cyclic peptides with D-Ala and D-His in the 32-position, respectively. The D-Ala$^{32}$ substitution significantly increases in vitro biopotency compared to the comparable analog with Gly$^{32}$, as does the D-His$^{32}$ substitution.

EXAMPLE 3C

The peptide (cyclo 29-32)[D-Leu$^{11}$, Nle$^{17}$, Glu$^{29}$, Lys$^{32}$]-sauvagine having the amino acid sequence: pGlu-Gly-Pro-Pro-Ile-Ser-Ile-Asp-Leu-Ser-D-Leu-Glu-Leu-Leu-Arg-Lys-Nle-Ile-Glu-Ile-Glu-Lys-Gln-Glu-Lys-Glu-Lys- Gln-Glu-Ala-Ala-Lys-Asn-Arg-Leu-Leu-Leu-Asp-Thr-Ile-NH$_2$ is synthesized using a procedure generally as set forth in Example 1. A portion of the peptide-resin is removed prior to cyclization, and it is cleaved and deprotected to provide the corresponding linear peptide. Amino acid analysis of the resultant, purified peptides is consistent with the amino acid sequence for the prepared peptides and confirms that the 40-residue peptide structures are obtained. Specific optical rotation at the Sodium D line of the cyclic peptide is measured, as previously described, as $[\alpha]_D^{22}$=−51.2°±1 (c=1 in 1% acetic acid, without correction for the presence of H$_2$O and TFA). It has a purity of about 98% confirmed by capillary zone electrophoresis. The LSIMS value of 4576.68 agrees with the calculated value of 4576.71. The peptide's biopotency, determined as previously described, is about 5.73 (2.61–13.51) times that of the standard peptide. The linear peptide is very significantly less biopotent.

Testing in accordance with the general procedure set forth hereinbefore shows that the cyclic peptide stimulates the secretion of ACTH and β-END-LI and causes a very significant lowering of blood pressure when administered peripherally.

The entire synthesis is repeated to produce the cyclic peptide with D-Ala in the 31-position and its linear counterpart, both of which are shortened by 2 residues at the N-terminus which is acetylated. The mass of the cyclic peptide is measured by Laser Desorption Mass Spectroscopy, (LDMS), and the value of 4436.8 agrees with the calculated value. The D-Ala$^{31}$ substitution in the cyclic peptide significantly increases biopotency compared to the Gly$^{31}$ cyclic analog; however, the D-Ala$^{31}$ linear peptide has a biopotency very significantly lower.

EXAMPLE 3D

The peptide (cyclo 30-33)[D-Phe$^{12}$, Nle$^{21,37,38}$, Glu$^{30}$, Lys$^{33}$]-fish CRF having the amino acid sequence: H-Ser- Glu-Glu-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu- Ala-Gln-Glu-Ala-His-Lys-Asn-Arg-Lys-Nle-Nle-Glu-Ile-Phe-NH$_2$ is synthesized using a procedure generally as set forth in Example 1. Testing in accordance with the general procedure set forth hereinbefore shows that it likewise stimulates the secretion of ACTH and β-END-LI and causes a very significant lowering of blood pressure when administered peripherally.

The synthesis is repeated to produce the cyclic peptide with D-His in the 32-position. The D-His$^{32}$ substitution significantly increases biopotency compared to His$^{32}$.

EXAMPLE 3E

The peptide (cyclo 30-33)[ Nle$^{6,14,18,24}$, D-Phe$^{12}$, Glu$^{30}$, D-Leu$^{32}$, Lys$^{33}$]-maggy urotensin having the amino acid sequence: H-Ser-Glu-Glu-Pro-Pro-Nle-Ser-Ile-Asp-Leu-Thr-D-Phe-His-Nle-Leu-Arg-Asn-Nle-Ile-His-Arg-Ala-Lys-Nle-Glu-Gly-Glu- Arg-Glu-Glu-Ala-D-Leu-Lys-Asn-Arg-Asn-Leu-Leu-Asp-Glu-Val-NH$_2$ is synthesized using a procedure generally as set forth in Example 1. Testing in accordance with the general procedure set forth hereinbefore shows that it likewise stimulates the secretion of ACTH and β-END-LI and causes a very significant lowering of blood pressure when administered peripherally.

The synthesis is repeated to produce the cyclic peptide with D-His in the 32-position. The D-His$^{32}$ substitution increases biopotency over that of the D-Leu$^{32}$ analog.

EXAMPLE 3F

The peptide (cyclo 30-33)[Ac-Pro$^4$, D-Phe$^{12}$, Nle$^{18,21}$, Glu$^{30}$, D-Ala$^{32}$, Lys$^{33}$]-carp urotensin(4-41) having the amino acid sequence: Ac-Pro-Pro-Ile-Ser-Ile-Asp-Leu-Thr-D-Phe-His-Leu-Leu-Arg-Asn-Nle-Ile-Glu-Nle-Ala-Arg-Asn-Glu-Asn-Gln-Arg-Glu-Glu- Ala-D-Ala-Lys-Asn-Arg-Lys-Tyr-Leu-Asp-Glu-Val-NH$_2$ is synthesized using a procedure generally as set forth in Example 1. Mass as measured by LDMS is 4539.5 which agrees with the calculated value. Testing in accordance with the general procedure set forth hereinbefore shows that it is significantly more potent than the Standard; it likewise stimulates the secretion of ACTH and β-END-LI and causes a very significant lowering of blood pressure when administered peripherally.

The synthesis is repeated to produce the comparable cyclic peptide with D-His in the 32-position. The D-His$^{32}$ substitution also significantly increases biopotency compared to the Standard.

EXAMPLE 3G

The peptide (cyclo 30-33)[ Nle6,14,18,24,38, D-Phe$^{12}$, Glu$^{30}$, D-Leu$^{32}$, Lys$^{33}$]-sole urotensin having the amino acid sequence: H-Ser-Glu-Glu-Pro-Pro-Nle-Ser-Ile-Asp-Leu-Thr-D-Phe-His-Nle-Leu-Arg-Asn-Nle-Ile-His-Arg-Ala-Lys-Nle-Glu-Gly-Glu- Arg-Glu-Glu-Ala-D-Leu-Lys-Asn-Arg-Asn-Leu-Nle-Asp-Glu-Val-NH$_2$ is synthesized using a procedure generally as set forth in Example 1. Testing in accordance with the general procedure set forth hereinbefore shows that it likewise stimulates the secretion of ACTH and β-END-LI and causes a very significant lowering of blood pressure when administered peripherally.

The synthesis is repeated to produce the cyclic peptide with D-His in the 32-position. The D-His$^{32}$ substitution increases biopotency compared to the cyclic D-Leu$^{32}$ analog.

EXAMPLE 3H

The peptide (cyclo 30-33)[ Nle$^{6,14,18,24}$, D-Phe$^{12}$, Glu$^{30}$, D-Gln$^{32}$, Lys$^{33}$]-flounder urotensin having the amino acid sequence: H-Ser-Glu-Asp-Pro-Pro-Nle-Ser-Ile-Asp-Leu-Thr-D-Phe-His-Nle-Leu-Arg-Asn-Nle-Ile-His-Arg-Ala-Lys-Nle-Glu-Gly-Glu- Arg-Glu-Glu-Ala-D-Gln-Lys-Asn-Arg-Asn-Leu-Leu-Asp-Glu-Val-NH$_2$ is synthesized using a procedure generally as set forth in Example 1. Testing in accordance with the general procedure set forth hereinbefore shows that it likewise stimulates the secretion of ACTH and β-END-LI and causes a very significant lowering of blood pressure when administered peripherally.

The synthesis is repeated to produce the cyclic peptide with D-His in the 32-position. The D-His$^{32}$ substitution increases biopotency compared to the cyclic D-Gln$^{32}$ analog.

EXAMPLE 3I

The peptide (cyclo 30-33)[D-Phe$^{12}$, Nle$^{21,38}$, Glu$^{30}$, Lys$^{33}$]-porcine CRF having the amino acid sequence: H-Ser-Glu-Glu-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu- Ala-Gln-Glu-Ala-His-Lys-Asn-Arg-Lys-Leu-Nle-Glu-Asn-Phe-NH$_2$ is synthesized using a procedure generally as set forth in Example 1. Testing in accordance with the general procedure set forth hereinbefore shows that it likewise stimulates the secretion of ACTH and β-END-LI and causes a very significant lowering of blood pressure when administered peripherally.

The synthesis is repeated to produce the cyclic peptide with D-His in the 32-position. The D-His$^{32}$ substitution significantly increases biopotency compared tyo the cyclic His32 analog.

EXAMPLE 4

The synthesis of (cyclo 30-33)[Ac-Pro$^4$, D-Phe$^{12}$, Nle$^{21,38}$, Glu$^{30}$, D-His$^{32}$, Orn$^{33}$]-r/hCRF(4-41) having the amino acid sequence: (cyclo 30-33)Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln- Leu-Ala-Gln-Glu-Ala-D-His-Orn-Asn-Arg-Lys-Leu-Nle-Glu-Ile-Ile-NH$_2$ is conducted as described in Example 1 above, except that residue-33 is Orn instead of Lys. Administration of the peptide stimulates the secretion of ACTH and β-END-LI.

EXAMPLE 4A

The synthesis of Example 4 is repeated, adding D-Tyr instead of acetyl at the N-terminus, to produce the following peptide: (cyclo 30-33)[D-Tyr$^3$, D-Phe$^{12}$, Nle$^{21,38}$, Glu$^{30}$, D-His$^{32}$, Orn$^{33}$]-r/hCRF(3-41), having the amino acid sequence: (cyclo 30-33)H-D-Tyr-Pro-Pro-Ile-Ser-Leu-Asp-Leu-Thr-D-Phe-His-Leu-Leu-Arg-Glu-Val-Leu-Glu-Nle-Ala-Arg-Ala-Glu- Gln-Leu-Ala-Gln-Glu-Ala-D-His-Orn-Asn-Arg-Lys-Leu-Nle-Glu-Ile-Ile-NH$_2$.

Administration of the peptide inhibits the secretion of ACTH and β-END-LI. A portion of the peptide is then iodinated with $^{125}$I to provide a ligand for use in competitive drug screening assays.

EXAMPLE 4B

The general synthesis of Example 1 is used to produce the following peptide: (cyclo 30-33)[Ac-Pro$^4$, D-Phe$^{12}$, Nle$^{21,38}$, Glu$^{30}$, D-His$^{32}$, Lys$^{33}$, Arg$^{36}$]-r/hCRF(4-41), having the amino acid sequence: (cyclo 30-33)Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln- Leu-Ala-Gln-Glu-Ala-D-His-Lys-Asn-Arg-Arg-Leu-Nle-Glu-Ile-Ile-NH$_2$. Administration of the peptide inhibits the secretion of ACTH and β-END-LI.

23

EXAMPLE 5

The peptide (cyclo 30-33)[Ac-Pro$^4$, D-Phe$^{12}$, Nle$^{21,38}$, Cys$^{30,33}$]r/hCRF(4-41) having the amino acid sequence: (cyclo 30-33)Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln- Cys-Ala-His-Cys-Asn-Arg-Lys-Leu-Nle-Glu-Ile-Ile-NH$_2$ is synthesized.

The synthesis protocol previously described herein is employed to produce the fully protected peptide-resin which is cleaved by HF. After precipitation and washing with diethyl ether (480 mL in 3 portions), the peptide is extracted with water (200 mL) and 5.0% AcOH (100 mL). The resulting solution is poured into 4.0 L of degassed water and the pH adjusted to 6.8–7.0 with NH$_4$OH. As the mixture becomes cloudy, CH$_3$CN (300 mL) is added to avoid precipitation. The mixture is then stirred at 4° C. under air atmosphere, and after 48 h, cyclization is complete (Ellman test). The pH is adjusted to 5.0 with AcOh, and the resulting solution is loaded on a Bio-Rex-70 column (120 mL). The column is washed with 0.5% AcOH (200 mL), and the peptide elutes with 50% AcOH. Fractions are collected, and those containing ninhydrin-positive material are diluted and lyophilized (80 mg).

Purification is performed in three steps. First the peptide is dissolved in buffer A (TEAP pH 2.25, 300 mL) and eluted by using as buffer B: 60% CH$_3$CN in A, with a gradient from 30 to 60% B in 60 minutes. Fractions are screened under isocratic conditions (53% B) and fractions containing the compound are pooled. In the second step, the pooled fractions are diluted with H$_2$O and eluted using buffer A: TEAP (pH 6.0) and B: 60% CH$_3$CN in A, with a gradient from 30 to 55% B in 60 minutes. Fractions are again screened under isocratic conditions (53% B), and the pooled fractions are diluted with H$_2$O and eluted using buffer A: 0.1% TFA/H$_2$O and B: 0.1% TFA in CH$_3$CN/H$_2$O (60:40), with a gradient from 30 to 60% B in 20 minutes. The fractions containing the product are pooled and lyophilized to yield the product peptide.

Administration of the peptide stimulates the secretion of ACTH and β-END-LI, and peripheral administration significantly lowers blood pressure.

EXAMPLE 6

The synthesis of Example 1 is repeated, substituting D-Pro for Pro$^4$ and D-Arg for D-His, to produce the following peptide: (cyclo 30-33)[Ac-D-Pro$^4$, D-Phe$^{12}$, Nle$^{21,38}$, Glu$^{30}$, D-Arg$^{32}$, Lys$^{33}$]-r/hCRF(4-41), having the amino acid sequence: (cyclo 30-33)Ac-D-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln- Leu-Ala-Gln-Glu-Ala-D-Arg-Lys-Asn-Arg-Lys-Leu-Nle-Glu-Ile-Ile-NH$_2$.

Administration of the peptide stimulates the secretion of ACTH and β-END-LI, and peripheral administration significantly lowers blood pressure.

EXAMPLE 6A

The synthesis of Example 1 is repeated, adding D-Tyr instead of Ac at the N-terminus and substituting D-Ala for D-His$^{32}$, to produce the following peptide: (cyclo 30-33)[D-Tyr$^3$, D-Phe$^{12}$, Nle$^{21,38}$, Glu$^{30}$, D-Ala$^{32}$, Lys$^{33}$]-r/hCRF(3-41), having the amino acid sequence: (cyclo 30-33)H-D-Tyr-Pro-Pro-Ile-Ser-Leu-Asp-Leu-Thr-D-Phe-His-Leu-Leu-Arg-Glu-Val-Leu-Glu-Nle-Ala-Arg-Ala-Glu- Gln-Leu-Ala-Gln-Glu-Ala-D-Ala-Lys-Asn-Arg-Lys-Leu-Nle-Glu-Ile-Ile-NH$_2$.

24

Administration of the peptide stimulates the secretion of ACTH and β-END-LI, and iv injection lowers blood pressure.

A portion of the peptide is iodinated with $^{125}$I to provide a ligand for use in drug screening assays for more effective CRF agonists.

EXAMPLE 6B

The synthesis of Example 1 is repeated, substituting D-Lys for D-His$^{32}$, to produce the following peptide: (cyclo 30-33)[Ac-Pro$^4$, D-Phe$^{12}$, Nle$^{21,38}$, Glu$^{30}$, D-Lys$^{32}$, Lys$^{33}$]-r/hCRF(4-41), having the amino acid sequence: (cyclo 30-33)Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln-Glu-Ala-D-Lys-Lys-Asn-Arg-Lys-Leu-Nle-Glu-Ile-Ile-NH$_2$.

Administration of the peptide stimulates the secretion of ACTH and β-END-LI, and iv injection lowers blood pressure.

EXAMPLE 6C

The synthesis of Example 1 is repeated, substituting D-Pro for Pro$^4$ and D-2Nal for D-His$^{32}$, to produce the following peptide: (cyclo 30-33)[Ac-D-Pro$^4$, D-Phe$^{12}$, Nle$^{21,38}$, Glu$^{30}$, D-2Nal$^{32}$, Lys$^{33}$]-r/hCRF(4-41), having the amino acid sequence: (cyclo 30-33)Ac-D-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln- Leu-Ala-Gln-Glu-Ala-D-2Nal-Lys-Asn-Arg-Lys-Leu-Nle-Glu-Ile-Ile-NH$_2$.

Administration of the peptide stimulates the secretion of ACTH and β-END-LI, and iv injection lowers blood pressure.

EXAMPLE 6D

The synthesis of Example 1 is repeated, substituting imBzlD-His for D-His$^{32}$ to produce the following peptide: (cyclo 30-33)[Ac-Pro$^4$, D-Phe$^{12}$, Nle$^{21,38}$, Glu$^{30}$, D-Amp$^{32}$, Lys$^{33}$]-r/hCRF(4-41), having the amino acid sequence: (cyclo 30-33)Ac-Pro-Pro-Ile-Ser-Leu-Asp-Leu-Thr-D-Phe-His-Leu-CML-Arg-Glu-Val-Leu-Glu-Nle-Ala-Arg-Ala-Glu-Gln- Leu-Ala-Gln-Glu-Ala-D-Amp-Lys-Asn-Arg-Lys-Leu-Nle-Glu-Ile-Ile-NH$_2$.

Administration of the peptide stimulates the secretion of ACTH and β-END-LI, and iv injection lowers blood pressure.

EXAMPLE 6E

The synthesis of Example 1 is repeated, substituting D-Iamp for D-His$^{32}$, to produce the following peptide: (cyclo 30-33)[Ac-Pro$^4$, D-Phe$^{12}$, Nle$^{21,38}$, Glu$^{30}$, D-Iamp$^{32}$, Lys$^{33}$]-r/hCRF(4-41), having the amino acid sequence; (cyclo 30-33)Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln- Leu-Ala-Gln-Glu-Ala-D-Iamp-Lys-Asn-Arg-Lys-Leu-Nle-Glu-Ile-Ile-NH$_2$.

Administration of the peptide stimulates the secretion of ACTH and β-END-LI, and iv injection lowers blood pressure.

EXAMPLE 7

The synthesis of (bicyclo 20-23, 30-33) [Ac-Pro$^4$, D-Phe$^{12}$, Nle$^{21,38}$, Lys$^{23,33}$, Glu$^{30}$, D-His$^{32}$]-r/hCRF(4-41) having the amino acid sequence: (bicyclo 20-23, 30-33)Ac-Pro-Pro-Ile-Ser-Leu-Asp-Leu-Thr-D-Phe-His-Leu-Leu- Arg-Glu-Val-Leu-Glu-Nle-Ala-Lys-Ala- Gln-Gln-Leu-Ala-Gln-Glu-Ala-D-His-Lys-Asn-Arg-Lys-Leu-Nle-Glu-Ile-Ile-NH$_2$ is conducted as generally described in Example I above, except that the lactam bridge between residues 30 and 33 is completed before residue 23 is added to the peptide-resin.

Administration of the peptide stimulates the secretion of ACTH and β-END-LI, and iv injection lowers blood pressure.

EXAMPLE 7A

The synthesis of (bicyclo 20-23, 30-33) [Ac-Pro$^4$, D-Phe$^{12}$, Nle$^{21,38}$, D-Ala$^{22}$, Lys$^{23,33}$, Glu$^{30}$, D-His$^{32}$]-r/hCRF(4-41) having the amino acid sequence: (bicyclo 20-23, 30-33)Ac-Pro-Pro-Ile-Ser-Leu-Asp-Leu-Thr-D-Phe-His-Leu-Leu-Arg-Glu-Val-Leu-Glu-Nle-D-Ala-Lys-Ala-Glu-Gln-Leu-Ala-Gln-Glu-Ala-D-His-Lys-Asn-Arg-Lys-Leu-Nle-Glu-Ile-Ile-NH$_2$ is conducted as generally described in Example 7 above, except that D-Ala is substituted for Ala$^{22}$.

Administration of the peptide stimulates the secretion of ACTH and β-END-LI, and iv injection lowers blood pressure.

EXAMPLE 8

The peptide (cyclo 30-33)[Ac-Pro$^4$, D-Phe$^{12}$, Nle$^{21,38}$, Cys$^{30,33}$, D-Amp$^{32}$]r/hCRF(4-41) having the amino acid sequence: Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln-Cys-) Ala-D-Amp-Cys-Asn-Arg-Lys-Leu-Nle-Glu-Ile-Ile-NH$_2$ is synthesized.

The synthesis protocol previously described in Example 5 is employed to produce the fully protected peptide-resin which is cleaved by HF, cyclized, purified, and then lyophilized to yield the product peptide.

The synthesis is repeated to yield the peptide. (cyclo 30-33)[Ac-Pro$^4$, D-Phe$^{12}$, Nle$^{21,38}$, Cys$^{30,33}$, D-Arg$^{32}$]r/hCRF(4-41).

Administration of either of the peptides stimulates the secretion of ACTH and β-END-LI.

EXAMPLE 8A

The peptide (cyclo 30-33)[Ac-Pro$^4$, D-Pro$^5$, D-Phe$^{12}$, Nle$^{18,21}$, Glu$^{30}$, D-His$^{32}$, Lys$^{33}$]-Carp Urotensin I(4-41) having the formula: Ac-Pro-D-Pro-Ile-Ser-Ile-Asp-Leu-Thr-D-Phe-His-Leu-Leu-Arg-Asn-Nle-Ile-Glu-Nle-Ala-Arg-)Asn-Glu-Asn-Gln-Arg-Glu-Glu-Ala-D-His-Lys-Asn-Arg-Lys-Tyr-Leu-Asp-Glu-Val-NH$_2$ is synthesized.

Administration shows that the cyclic compound relieves inflammation.

EXAMPLE 8B

The peptide (cyclo 29-32)[Ac-Pro$^3$, D-Pro$^4$, D-Leu$^{11}$, Nle$^{17}$, Glu$^{29}$, D-His$^{31}$, Lys$^{32}$]-sauvagine(3-40) having the formula: Ac-Pro-D-Pro-Ile-Ser-Ile-Asp-Leu-Ser-D-Leu-Glu-Leu-Leu-Arg-Lys-Nle-Ile-Glu-Ile-Glu-Lys-Gln-Glu-Lys-Glu- Lys-Gln-Glu-Ala-D-His-Lys-Asn-Arg-Leu-Leu-Leu-Asp-Thr-Ile-NH$_2$ is synthesized.

Administration shows that the cyclic compound relieves inflammation.

EXAMPLE 8C

The peptide (cyclo 30-33)[Ac-Pro$^4$, D-Pro$^5$, D-Phe$^{12}$, Nle$^{18,21}$, Glu$^{30}$, D-His$^{32}$, Lys$^{33}$]-α-helical CRF(4-41) having the formula: Ac-Pro-D-Pro-Ile-Ser-Leu-Asp-Leu-Thr-D-Phe-His-Leu-Leu-Arg-Glu-Nle-Leu-Glu-Nle-Ala-Lys-Ala-Glu-Gln-Glu-Ala-Glu-Glu-Ala-D-His-Lys-Asn-Arg-Leu-Leu-Leu-Glu-Glu-Ala-NH$_2$ is synthesized.

Administration shows that the cyclic compound relieves inflammation.

EXAMPLE 8D

The general synthesis of Example 1 is used to produce the following peptide: (cyclo 30-33)[Ac-Pro$^4$, D-Pro$^5$, D-Phe$^{12}$, Nle$^{21,38}$, Glu$^{30}$, D-His$^{32}$, Lys$^{33}$]-r/hCRF(4-41), having the amino acid sequence: (cyclo 30-33)Ac-Pro-D-Pro-Ile-Ser-Leu-Asp-Leu-Thr-D-Phe-His-Leu-Leu-Arg-Glu-Val-Leu-Glu-Nle-Ala-Arg-Ala-Glu-Gln- Leu-Ala-Gln-Glu-Ala-D-His-Lys-Asn-Arg-Lys-Leu-Nle-Glu-Ile-Ile-NH$_2$.

Administration of the peptide relieves inflammation.

EXAMPLE 8E

The peptide (cyclo 30-33)[Ac-Pro$^4$, D-Pro$^5$, D-Phe$^{12}$, Nle$^{18,21}$, Glu$^{30}$, D-His$^{32}$, Lys$^{33}$]-sucker urotensin(4-41) having the amino acid sequence: Ac-Pro-D-Pro-Ile-Ser-Ile-Asp-Leu-Thr-D-Phe-His-Leu-Leu-Arg-Asn-Nle-Ile-Glu-Nle-Ala-Arg-Ile-Glu-Asn-Glu-Arg-Glu-Glu-Ala-D-His-Lys-Asn-Arg-Lys-Tyr-Leu-Asp-Glu-Val-NH$_2$ is synthesized using a procedure generally as set forth in Example 1. Amino acid analysis of the resultant, purified peptide is consistent with the amino acid sequence for the prepared peptide and confirms that the 38-residue peptide structure is obtained.

Administration of the cyclic peptide relieves inflammation.

EXAMPLE 8F

The peptide (cyclo 30-33)[Ac-Pro$^4$, D-Pro$^5$, D-Phe$^{12}$, Nle$^{21,38}$, Glu$^{30}$, D-His$^{32}$, Lys$^{33}$]-oCRF(4-41) having the amino acid sequence: Ac-Pro-D-Pro-Ile-Ser-Leu-Asp-Leu-Thr-D-Phe-His-Leu-Leu-Arg-Glu-Val-Leu-Glu-Nle-Thr-Lys-Ala-Asp-Gln-Leu-Ala-Gln-Glu-Ala-D-His-Lys-Asn-Arg-Lys-Leu-Nle-Asp-Ile-Ala-NH$_2$ is synthesized using a procedure generally as set forth in Example 1.

Administration of the cyclic peptide relieves inflammation.

EXAMPLE 9

The synthesis of Example 1 is repeated, substituting CαMeLeu for Leu$^{15}$, to produce the following peptide: (cyclo 30-33)[Ac-Pro$^4$, D-Phe$^{12}$, CML$^{15}$, Nle$^{21,38}$, Glu$^{30}$, D-His$^{32}$, Lys$^{33}$]-r/hCRF(4-41), having the amino acid sequence: (cyclo 30-33)Ac-Pro-Pro-Ile-Ser-Leu-Asp-Leu-Thr-D-Phe-His-Leu-CML-Arg-Glu-Val-Leu-Glu-Nle-Ala-Arg-Ala-Glu-Gln- Leu-Ala-Gln-Glu-Ala-D-His-Lys-Asn-Arg-Lys-Leu-Nle-Glu-Ile-Ile-NH$_2$.

Administration of the peptide stimulates the secretion of ACTH and β-END-LI, and iv injection lowers blood pressure.

EXAMPLE 9A

The synthesis of Example 1 is repeated, but this time substituting CαMeLeu for Leu$^{14}$, to produce the following peptide: (cyclo 30-33)[Ac-Pro$^4$, D-Phe$^{12}$, CML$^{14}$, Nle$^{21,38}$, Glu$^{30}$, D-His$^{32}$, Lys$^{33}$]-r/hCRF(4-41), having the amino acid sequence: (cyclo 30-33)Ac-Pro-Pro-Ile-Ser-Leu-Asp-Leu-Thr-D-Phe-His-CML-Leu-Arg-Glu-Val-Leu-Glu-Nle-Ala-Arg-Ala-Glu-Gln- Leu-Ala-Gln-Glu-Ala-D-His-Lys-Asn-Arg-Lys-Leu-Nle-Glu-Ile-Ile-NH$_2$.

27

Administration of the peptide stimulates the secretion of ACTH and β-END-LI, and iv injection lowers blood pressure.

EXAMPLE 9B

The synthesis of Example 1 is repeated again, but this time substituting CαMeLeu for Leu$^{19}$, to produce the following peptide: (cyclo 30-33)[Ac-Pro$^4$, D-Phe$^{12}$, CML$^{19}$, Nle$^{21,38}$, Glu$^{30}$, D-His$^{32}$, Lys$^{33}$]-r/hCRF (4-41), having the amino acid sequence: (cyclo 30-33)Ac-Pro-Pro-Ile-Ser-Leu-Asp-Leu-Thr-D-Phe-His-Leu-Leu-Arg-Glu-Val-CML-Glu-Nle-Ala-Arg-Ala-Glu-Gln- Leu-Ala-Gln-Glu-Ala-D-His-Lys-Asn-Arg-Lys-Leu-Nle-Glu-Ile-Ile-NH$_2$.

Administration of the peptide stimulates the secretion of ACTH and β-END-LI, and iv injection lowers blood pressure.

EXAMPLE 9C

The synthesis of Example 1 is repeated once more, substituting CαMeLeu for Leu$^{27}$, to produce the following peptide: (cyclo 30-33)[Ac-Pro$^4$, D-Phe$^{12}$, Nle$^{21,38}$, CML$^{27}$, Glu$^{30}$, D-His$^{32}$, Lys$^{33}$]-r/hCRF(4-41), having the amino acid sequence: (cyclo 30-33)Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln- CML-Ala-Gln-Glu-Ala-D-His-Lys-Asn-Arg-Lys-Leu-Nle-Glu-Ile-Ile-NH$_2$.

Administration of the peptide stimulates the secretion of ACTH and β-END-LI, and iv injection lowers blood pressure.

EXAMPLE 9D

The synthesis of Example 1 is repeated, substituting CαMeLeu for Leu$^{37}$, to produce the following peptide: (cyclo 30-33)[Ac-Pro$^4$, D-Phe$^{12}$, Nle$^{21,38}$, Glu$^{30}$, D-His$^{32}$, Lys$^{33}$, CML$^{37}$]-r/hCRF(4-41), having the amino acid sequence: (cyclo 30-33)Ac-Pro-Pro-Ile-Ser-Leu-Asp-Leu-Thr-D-Phe-His-Leu-Leu-Arg-Glu-Val-Leu-Glu-Nle-Ala-Arg- Ala-Glu-Gln-Leu-Ala-Gln-Glu-Ala-D-His-Lys-Asn-Arg-Lys-CML-Nle-Glu-Ile-Ile-NH$_2$.

Administration of the peptide stimulates the secretion of ACTH and β-END-LI, and iv injection lowers blood pressure.

EXAMPLE 9E

The synthesis of Example 1 is repeated again, but this time substituting CαMeLeu for Glu$^{17}$, to produce the following peptide: (cyclo 30-33)[Ac-Pro$^4$, D-Phe$^{12}$, CML$^{17}$, Nle$^{21,38}$, Glu$^{30}$, D-His$^{32}$, Lys$^{33}$]-r/hCRF (4-41), having the amino acid sequence: (cyclo 30-33)Ac-Pro-Pro-Ile-Ser-Leu-Asp-Leu-Thr-D-Phe-His-Leu-Leu-Arg-CML-Val-Leu-Glu-Nle-Ala-Arg-Ala-Glu-Gln- Leu-Ala-Gln-Glu-Ala-D-His-Lys-Asn-Arg-Lys-Leu-Nle-Glu-Ile-Ile-NH$_2$.

Administration of the peptide stimulates the secretion of ACTH and β-END-LI, and iv injection lowers blood pressure.

EXAMPLE 10

Using the procedure set forth in Example 1, the following peptides are also prepared:

(c 30–33) [Acetyl-Ser$^1$, D-Phe$^{12}$, Nle$^{21,38}$, Glu$^{30}$, Lys$^{33}$]-r/hCRF
" [D-Phe$^{12}$, Glu$^{30}$, Lys$^{33}$]-oCRF

28

-continued

" [D-Phe$^{12}$, D-Ala$^{24}$, Glu$^{30}$, Lys$^{33}$]-r/hCRF(4-41)
" [D-Phe$^{12}$, Nle$^{21}$, Aib$^{34}$, Glu$^{30}$, Lys$^{33}$]-oCRF
" [Formyl-Ser$^1$, D-Phe$^{12}$, Nle$^{21,38}$, Glu$^{30}$, Lys$^{33}$]-r/hCRF
" [CML$^{17,37}$, Glu$^{30}$, Lys$^{33}$]-oCRF
" [D-Tyr$^{12}$, CML$^{17}$, Glu$^{30}$, Lys$^{33}$]-r/hCRF (2-41)
" [D-3Pal$^{12}$, Nle$^{21,38}$, Glu$^{30}$, Lys$^{33}$]-oCRF
" [Glu$^{30}$, D-His$^{32}$, Lys$^{33}$, Aib$^{34}$]-oCRF
" [D-Phe$^{12}$, D-Ala$^{24}$, Glu$^{30}$, D-His$^{32}$, Lys$^{33}$]-r/hCRF (6-41)
" [Nle$^{21}$, Aib$^{29}$, Glu$^{30}$, D-His$^{32}$, Lys$^{33}$]-oCRF
" [Acrylyl-Glu$^2$, Nle$^{21,38}$, Glu$^{30}$, D-His$^{32}$, Lys$^{33}$]-r/hCRF (2-41)
" [Nle$^{18,21}$, Glu$^{30}$, D-His$^{32}$, Lys$^{33}$]-AHC
" [D-Pro$^4$, D-Phe$^{12}$, Nle$^{18,21}$, Glu$^{30}$, Lys$^{33}$]-AHC (4-41)
" [D-Tyr$^3$, Nle$^{18}$, Nva$^{21}$, Glu$^{30}$, Lys$^{33}$]-AHC
" [CML$^{17}$, Nle$^{18,21}$, Glu$^{30}$, Lys$^{33}$]-AHC
" [D-Phe$^{12}$, CML$^{17}$, Glu$^{30}$, Lys$^{33}$]-AHC
" [D-4ClPhe$^{12}$, Glu$^{30}$, Lys$^{33}$, CML$^{37}$]-AHC
" [Nle$^{18,21}$, Glu$^{30}$, Lys$^{33}$, CML$^{37}$]-AHC
" [CML$^{17}$, Glu$^{30}$, Lys$^{33}$]-AHC
" [Tyr$^{13}$, Glu$^{30}$, Lys$^{33}$]-AHC
" [Aib$^{19}$, Nle$^{21}$, Glu$^{30}$, D-Arg$^{32}$, Lys$^{33}$, CML$^{37}$]-oCRF
" [D-2Nal$^{12}$, Nle$^{21,38}$, Aib$^{29}$, Glu$^{30}$, Lys$^{33}$, CML$^{37}$]-oCRF
" [Nle$^{21,38}$, Glu$^{30}$, Lys$^{33}$, CML$^{37}$]-oCRF These peptides are biopotent in stimulating the secretion of ACTH and β-END-LI and in decreasing systemic blood pressure when administered intravenously.

EXAMPLE 11

Using the procedure set forth in Example 1, the following peptides are also prepared:

(c 30–33) [Acetyl-Ser$^1$, D-Phe$^{12}$, Nle$^{21,38}$, Glu$^{30}$, D-His$^{32}$, Lys$^{33}$]-r/hCRF
" [D-Phe$^{12}$, Glu$^{30}$, D-2Nal$^{32}$, Lys$^{33}$]-oCRF
" [D-Phe$^{12}$, D-Ala$^{24}$, Glu$^{30}$, D-Ala$^{32}$, Lys$^{33}$]-r/hCRF (4-41)
" [D-Phe$^{12}$, Nle$^{21}$, Glu$^{30}$, D-His$^{32}$, Lys$^{33}$, Aib$^{34}$]-oCRF
" [CML$^{17,37}$, Glu$^{30}$, D-2Nal$^{32}$, Lys$^{33}$]-oCRF
" [D-Tyr$^{12}$, CML$^{17}$, Glu$^{30}$, D-Aib$^{32}$, Lys$^{33}$]-r/hCRF (2-41)
" [D-3Pal, Nle$^{21,38}$, Glu$^{30}$, D-Ala$^{32}$, Lys$^{33}$]-oCRF
" [Glu$^{30}$, D-Iamp$^{32}$, Lys$^{33}$, Aib$^{34}$]-oCRF
" [D-Phe$^{12}$, D-Ala$^{24}$, Glu$^{30}$, D-Amp$^{32}$, Lys$^{33}$]-r/hCRF (6-41)
" [Nle$^{21}$, Aib$^{29}$, Glu$^{30}$, D-Aph$^{32}$, Lys$^{33}$]-oCRF
" [Acr-Glu$^2$, Nle$^{21,38}$, Glu$^{30}$, imBzlD-His$^{32}$, Lys$^{33}$]-r/hCRF (2-41)
" [Nle$^{18,21}$, D-Glu$^{20}$, Glu$^{30}$, D-3Pal$^{32}$, Lys$^{33}$]-AHC
" [D-Pro$^4$, D-Phe$^{12}$, Nle$^{18,21}$, Glu$^{30}$, D-Ala$^{32}$, Lys$^{33}$]-AHC (4-41)
" [CML$^{17}$, Nle$^{18,21}$, Glu$^{30}$, D-Ala$^{32}$, Lys$^{33}$]-AHC
" [D-Phe$^{12}$, CML$^{17}$, Glu$^{30}$, D-2Nal$^{32}$, Lys$^{33}$]-AHC
" [Nle$^{18,21}$, Glu$^{30}$, D-2Nal$^{32}$, Lys$^{33}$, CML$^{37}$]-AHC
" [CML$^{17}$, Glu$^{30}$, D-2Nal$^{32}$, Lys$^{33}$]-AHC
" [Tyr$^{13}$, Glu$^{30}$, D-Ala$^{32}$, Lys$^{33}$]-AHC
(c 30–33) [Aib$^{19}$, Nle$^{21}$, Glu$^{30}$, D-Tyr$^{32}$, Lys$^{33}$, CML$^{37}$]-oCRF
" [Nle$^{21,38}$, Glu$^{30}$, D-Arg$^{32}$, Lys$^{33}$, CML$^{37}$]-oCRF These peptides are biopotent in stimulating the secretion of ACTH and β-END-LI and in decreasing systemic blood pressure when administered intravenously.

EXAMPLE 12

Using the procedure as generally set forth in Example 1, the following CRF agonist peptides are also prepared:

(c 30–33) [Glu$^{30}$, D-His$^{32}$, Lys$^{33}$]-AHC (4-41)
" [CML$^{17}$, Glu$^{30}$, D-Ala$^{32}$, Lys$^{33}$]-oCRF (4-41)
" [CML$^{14}$, D-Glu$^{20}$, Nle$^{21,38}$, Glu$^{30}$, D-Tyr$^{32}$, Lys$^{33}$]-r/hCRF (4-41)
" [D-2Nal$^{12}$, CML$^{14}$, Glu$^{30}$, D-2Nal$^{32}$, Lys$^{33}$]-oCRF (3-41)
" [CML$^{17}$, Nle$^{18,21}$, Glu$^{30}$, D-Arg$^{32}$, Lys$^{33}$]-AHC (2-41)
" [D-Glu$^{20}$, Glu$^{30}$, D-Leu$^{32}$, Lys$^{33}$]-r/hCRF (4-41)

-continued

" [D-Phe$^{12}$, CML$^{17,37}$, Nle$^{21}$, Glu$^{30}$, Tyr$^{32}$, Lys$^{33}$]-oCRF (3-41)
" [D-4Cpa$^{12}$, Glu$^{30}$, Arg$^{32}$, Lys$^{33}$]-AHC (2-41)
" [D-Tyr$^{12}$, CML$^{15}$, Nle$^{21,38}$, Glu$^{30}$, D-Val$^{32}$, Lys$^{33}$]-r/hCRF
" [D-Glu$^{20}$, Nle$^{21,38}$, Glu$^{30}$, D-Ser$^{32}$, Lys$^{33}$]-r/hCRF (4-41)
" [Ac-Thr, D-Leu$^{12}$, CML$^{17,37}$, Nle$^{21,38}$, Glu$^{30}$, D-Asn$^{32}$, Lys$^{33}$]-r/hCRF (3-41)
" [Nle$^{18,21}$, Glu$^{30}$, D-4Cpa$^{32}$, Lys$^{33}$]-AHC (2-41)
" [CML$^{17}$, D-Glu$^{20}$, Glu$^{30}$, D-3Pal$^{32}$, Lys$^{33}$, Aib$^{34}$]-r/hCRF (4-41)
" [CML$^{17,37}$, Nle$^{21,38}$, Glu$^{30}$, Aib$^{32}$, Lys$^{33}$]-r/hCRF (3-41)
" [D-Phe$^{12}$, CML$^{19}$, Glu$^{30}$, D-Lys$^{32}$, Lys$^{33}$]-r/hCRF (4-41)
(c 30–33) [D-Pal$^{12}$, Nle$^{21}$, CML$^{27,37}$, Glu$^{30}$, D-Phe$^{32}$, Lys$^{33}$]-oCRF (2-41)
" [D-Glu$^{20}$, CML$^{27}$, Glu$^{30}$, D-Gln$^{32}$, Lys$^{33}$]-AHC (4-41)
" [Acr-Glu$^{3}$, D-Phe$^{12}$, Nle$^{21,38}$, Glu$^{30}$, Ala$^{32}$, Lys$^{33}$]-r/hCRF (3-41)
" [Ac-Pro$^{4}$, D-Phe$^{12}$, Nle$^{21,38}$, Glu$^{30}$, D-Orn$^{32}$, Lys$^{33}$]-r/hCRF (4-41)
" [D-Phe$^{12}$, Nle$^{21,38}$, Glu$^{30}$, D-(Et)$_2$Arg$^{32}$, Lys$^{33}$]-r/hCRF
" [Ac-Pro$^{4}$, D-Phe$^{12}$, Nle$^{21,38}$, Glu$^{30}$, D-Dbu$^{32}$, Lys$^{33}$]-r/hCRF (4-41)
" [Ac-Pro$^{4}$, D-Phe$^{12}$, Nle$^{21,38}$, Glu$^{30}$, D-Lys$^{32}$, Lys$^{33}$]-r/hCRF (4-41)
" [Ac-Pro$^{4}$, D-Phe$^{12}$, Nle$^{21,38}$, Glu$^{30}$, D-Aph$^{32}$, Lys$^{33}$]-r/hCRF (4-41)
" [Ac-Pro$^{4}$, D-Phe$^{12}$, Nle$^{21,38}$, Glu$^{30}$, D-Hly$^{32}$, Lys$^{33}$]-r/hCRF (4-41)
" [Nph-Pro$^{4}$, D-Phe$^{12}$, Nle$^{21,38}$, Glu$^{30}$, D-Dpr$^{32}$, Lys$^{33}$]-r/hCRF (4-41)
" [Ac-Pro$^{4}$, D-Phe$^{12}$, Nle$^{21,38}$, Glu$^{30}$, D-Amp$^{32}$, Lys$^{33}$]-r/hCRF (4-41)
" [Ac-Pro$^{4}$, D-Phe$^{12}$, Nle$^{21,38}$, Glu$^{30}$, D-Lys(isopropyl)$^{32}$, Lys$^{33}$]-r/hCRF (4-41)
" [Ac-Pro$^{4}$, D-Phe$^{12}$, Nle$^{21,38}$, Glu$^{30}$, D-Amp(isopropyl)$^{32}$, Lys$^{33}$]-r/hCRF (4-41)
" [Ac-Pro$^{4}$, D-Phe$^{12}$, Nle$^{21,38}$, Glu$^{30}$, D-Aph(methyl)$^{32}$, Lys$^{33}$]-r/hCRF (4-41)
" [Flu-Pro$^{4}$, D-Phe$^{12}$, Nle$^{21,38}$, Glu$^{30}$, D-Har(ethyl)$^{32}$, Lys$^{33}$]-r/hCRF (4-41)
" [Ac-Pro$^{4}$, D-Phe$^{12}$, Nle$^{21,38}$, Glu$^{30}$, D-Amp(methyl)$^{32}$, Lys$^{33}$]-r/hCRF (4-41)
" [Ac-Pro$^{4}$, D-Phe$^{12}$, Nle$^{21,38}$, Glu$^{30}$, D-Dpr(isopropyl)$^{32}$, Lys$^{33}$]-r/hCRF (4-41)
" D-Phe$^{12}$, Nle$^{21,38}$, CML$^{27}$, Glu$^{30}$, D-Thr$^{32}$, Lys$^{33}$]-r/hCRF (3-41)
(bc 20–23, [Ac-Pro$^{4}$, D-Phe$^{12}$, Nle$^{21,38}$, Lys$^{23,33}$, Glu$^{30}$, Gly$^{32}$]-r/hCRF (4-41)
30–33)

These peptides are biopotent in stimulating the secretion of ACTH and β-END-LI in response to various stimuli and in decreasing systemic blood pressure when administered iv.

EXAMPLE 13

Using the procedure as generally set forth in Example 1, the following CRF agonist peptides are also prepared:

(c 30–33) [D-Pro$^{5}$, Nle$^{21}$, Aib$^{29}$, Glu$^{30}$, D-Aph$^{32}$, Lys$^{33}$]-oCRF
" [D-Pro$^{5}$, Nle$^{21,38}$, Glu$^{30}$, imbzlD-His$^{32}$, Lys$^{33}$]-r/hCRF (4-41)
" [D-Pro$^{5}$, Nle$^{18,21}$, Glu$^{30}$, D-His$^{32}$, Lys$^{33}$]-AHC
" [D-Pro$^{5}$, D-Phe$^{12}$, Nle$^{18,21}$, Glu$^{30}$, D-Ala$^{32}$, Lys$^{33}$]-AHC (4-41)
" [D-Pro$^{5}$, Nle$^{18,21}$, Glu$^{30}$, D-2Nal$^{32}$, Lys$^{33}$, CML$^{37}$]-AHC
" [D-Pro$^{5}$, CML$^{17}$, Glu$^{30}$, D-2Nal$^{32}$, Lys$^{33}$]-AHC
" [D-Pro$^{5}$, Nle$^{21,38}$, Glu$^{30}$, D-Arg$^{32}$, Lys$^{33}$, CML$^{37}$]-oCRF
" [D-Pro$^{5}$, Glu$^{30}$, D-His$^{32}$, Lys$^{33}$]-AHC (4-41)
" [D-Pro$^{5}$, Glu$^{30}$, D-Leu$^{32}$, Lys$^{33}$]-r/hCRF (4-41)
" [D-Pro$^{5}$, D-4Cpa$^{12}$, Glu$^{30}$, Arg$^{32}$, Lys$^{33}$]-AHC (2-41)
" [D-Pro$^{5}$, Nle$^{21,38}$, Glu$^{30}$, D-Ser$^{32}$, Lys$^{33}$]-r/hCRF (4-41)
" [D-Pro$^{5}$, Nle$^{18k,21}$, Glu$^{30}$, D-4Cpa$^{32}$, Lys$^{33}$]-AHC (2-41)
" [D-Pro$^{5}$, CML$^{17}$, Nle$^{21,38}$, Glu$^{30}$, Lys$^{33}$]-r/hCRF (3-41)
" [D-Pro$^{5}$, D-Phe$^{12}$, CML$^{19}$, Glu$^{30}$, D-Lys$^{32}$, Lys$^{33}$]-r/hCRF (4-41)
" [D-Pro$^{5}$, CML$^{27}$, Glu$^{30}$, D-Gln$^{32}$, Lys$^{33}$]-AHC (4-41)
(c 30–33) [Ac-Glu$^{3}$, D-Pro$^{5}$, D-Phe$^{12}$, Nle$^{21,38}$, Glu$^{30}$, Ala$^{32}$, Lys$^{33}$]-r/hCRF (3-41)
" [Ac-Pro$^{4}$, D-Pro$^{5}$, D-Phe$^{12}$, Nle$^{21,38}$, Glu$^{30}$, D-Orn$^{32}$, Lys$^{33}$]-r/hCRF (4-41)
" [Ac-Pro$^{4}$, D-Pro$^{5}$, D-Phe$^{12}$, Nle$^{21,38}$, Glu$^{30}$, D-Dbu$^{32}$, Lys$^{33}$]-r/hCRF (4-41)
" [Ac-Pro$^{4}$, D-Pro$^{5}$, D-Phe$^{12}$, Nle$^{21,38}$, Glu$^{30}$, D-Lys$^{32}$, Lys$^{33}$]-r/hCRF (4-41)
" [Ac-Pro$^{4}$, D-Pro$^{5}$, D-Phe$^{12}$, Nle$^{21,38}$, Glu$^{30}$, D-Aph$^{32}$, Lys$^{33}$]-r/hCRF (4-41)
" [Ac-Pro$^{4}$, D-Pro$^{5}$, D-Phe$^{12}$, Nle$^{21,38}$, Glu$^{30}$, D-Hly$^{32}$, Lys$^{33}$]-r/hCRF (4-41)
" [Ac-Pro$^{4}$, D-Pro$^{5}$, D-Phe$^{12}$, Nle$^{21,38}$, Glu$^{30}$, D-Amp$^{32}$, Lys$^{33}$]-r/hCRF (4-41)
" [Ac-Pro$^{4}$, D-Pro$^{5}$, D-Phe$^{12}$, Nle$^{21,38}$, Glu$^{30}$, D-Lys(isopropyl)$^{32}$, Lys$^{33}$]-r/hCRF (4-41)
" [Ac-Pro$^{4}$, D-Pro$^{5}$, D-Phe$^{12}$, Nle$^{21,38}$, Glu$^{30}$, D-Iamp$^{32}$, Lys$^{33}$]-r/hCRF (4-41)
" [Ac-Pro$^{4}$, D-Pro$^{5}$, D-Phe$^{12}$, Nle$^{21,38}$, Glu$^{30}$, D-Aph(methyl)$^{32}$, Lys$^{33}$]-r/hCRF (4-41)
" [Ac-Pro$^{4}$, D-Pro$^{5}$, D-Phe$^{12}$, Nle$^{21,38}$, Glu$^{30}$, D-Har(ethyl)$^{32}$, Lys$^{33}$]-r/hCRF (4-41)
" [Ac-Pro$^{4}$, D-Pro$^{5}$, D-Phe$^{12}$, Nle$^{21,38}$, Glu$^{30}$, D-Amp(methyl)$^{32}$, Lys$^{33}$]-r/hCRF (4-41)
" [Ac-Pro$^{4}$, D-Pro$^{5}$, D-Phe$^{12}$, Nle$^{21,38}$, Glu$^{30}$, D-Dpr(isopropyl)$^{32}$, Lys$^{33}$]-r/hCRF (4-41)
(bc 20–23, [Ac-Pro$^{4}$, D-Pro$^{5}$, D-Phe$^{12}$, Nle$^{21,38}$, 30–33) Lys$^{23,33}$, Glu$^{30}$, D-His$^{32}$]-r/hCRF (4-41)

These peptides are biopotent in relieving inflammation.

CRF profoundly stimulates the pituitary-adrenalcortical axis, and acts within the brain to mediate a wide range of stress responses. CRF agonists should be useful to stimulate the functions of this axis in some types of patients with low endogenous glucocorticoid production. For example, CRF agonists should be useful in restoring pituitary-adrenal function in patients having received exogenous glucocorticoid therapy whose pituitary-adrenalcortical functions remain suppressed.

Most other regulatory peptides have been found to have effects upon the endocrine system, the central nervous system and upon the gastrointestinal tract. Because ACTH and β-END-LI secretion is the "sine qua non" of mammal's response to stress, it was not surprising that CRF has significant effects on the brain as a mediator of many of the body's stress responses. Accordingly, CRF agonists are considered to also find application in modifying the mood, learning, memory and behavior of normal and mentally disordered individuals. Because CRF elevates the levels of ACTH, β-END, β-lipotropin, other pro-opiomelanocortin gene products and corticosterone, administration of these CRF agonists can be used to induce the effects of the foregoing POMC-derived peptides on the brain to thereby influence memory, mood, pain appreciation, etc., and more specifically, alertness, depression and/or anxiety, and also their effects peripherally. For example, when administered directly into the ventricles, CRF agonists increase physical activity and improve learning performance in rats and thus may function as a natural stimulant.

Because it is known that the addition of CRF into the left atrium of an isolated perfused heart induces a prolonged dilatory effect on coronary arteries, transiently produces a positive inotropic effect and stimulates the secretion of atrial natriuretic peptide, CRF agonists may be used for regulating cardiac perfusion. Other vascular beds, such as the superior mesenteric, may also be dilated by CRF analogs.

CRF agonist peptides of the invention are also therapeutically useful to modulate blood flow in many various vascular beds, and particularly in desired tissues and organs. CRF analogs are of use for increasing blood flow to the gastrointestinal tract of animals, particularly humans and other mammals, as they are shown to dilate the mesenteric vascular bed. CRF has been shown to modulate vascular permeability (Wei E. T. et al., "Peripheral anti-inflammatory actions of corticotropin-releasing factor", pp. 258–276, *Corticotropin-Releasing Factor* (Ciba Foundation Symposium 172) John Wiley & Sons, 1993), and these CRF agonists will also reduce vascular leakage and have a salutary effect on injury- or surgery-induced tissue swelling and inflammation. Therefore, CRF agonists can be administered parenterally to decrease inflammation, swelling and edema and to reduce fluid loss following heat injury.

oCRF, r/hCRF, urotensin I and sauvagine have been shown to inhibit gastric acid production, and the CRF agonists of the invention are considered to also be effective in the treatment of gastric ulcers by reducing gastric acid production and/or inhibiting certain gastro-intestinal functions in a mammal. CRF agonists will be effective in increasing intestinal transit rate and useful in the treatment of acute constipation.

A number of direct stimulatory effects of CRF on the GI tract have earlier been described. For example, CRF acts on the gut in vitro to depolarize myenteric neurons in the small intestine. The results of in vivo studies with intravenously administered CRF and CRF antagonists have been consistent with the observed effect of CRF to control gastric emptying and intestinal motility. The CRF agonist peptides of the invention are considered useful in treating intestinal and gastrointestinal disorders, such as irritable bowel syndrome. CRF antagonists have previously been used to therapeutically treat irritable bowel syndrome, and CRF antagonists are also useful to treat spastic colon and Crohn's disease. It is felt that highly potent CRF agonists will also be able to achieve these effects of the present CRF antagonists.

These CRF agonist peptides may also be used to evaluate hypothalamic pituitary adrenal function in mammals with suspected endocrine or central nervous system pathology by suitable administration followed by monitoring bodily functions. For example, administration may be used as a diagnostic tool to evaluate Cushing's disease and affective disorders, such as depressive illness.

CRF agonists or the nontoxic addition salts thereof, combined with a pharmaceutically acceptable carrier to form a pharmaceutical composition, may be administered to mammals, including humans, either intravenously, subcutaneously, intramuscularly, percutaneously, e.g. intranasally, intracerebro-ventricularly or orally. The peptides should be at least about 90% pure and preferably should have a purity of at least about 98%; however, lower purities are effective and may well be used with mammals other than humans. This purity means that the intended peptide constitutes the stated weight % of all like peptides and peptide fragments present. Administration to humans should be under the direction of a physician for the various uses outlined above. Administration may be in a variety of dosage forms such as tablets, lozenges, powders, syrups, injectable solutions and the like. The required dosage will vary with the particular condition being treated, with the severity of the condition and with the duration of desired treatment, and multiple dosages may be used for a single day. For parental administration, solutions in peanut oil, in aqueous propylene glycol, or in sterile aqueous solution may be employed. Such aqueous solutions, which are suitably buffered, are especially suitable for intravenous, intramuscular, subcutaneous and intraperitoneal administration. Sterile aqueous media are readily available.

Such peptides are often administered in the form of pharmaceutically acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, hydriodide, cinnamate, sulphate, sulfamate, sulfonate, phosphate, tannate, oxalate, fumarate, gluconate, alginate, maleate, acetate, citrate, benzoate, succinate, malate, ascorbate, tartrate and the like which can be prepared in a conventional manner. If the active ingredient is to be administered in tablet form, the tablet may contain a binder or excipient, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician in single or multiple doses, and pharmaceutical compositions will usually contain the peptide in conjunction with a conventional, pharmaceutically-acceptable carrier. The effective dosage generally depends on the intended route of administration and other factors such as age and weight of the patient, as generally known to a physician, and also upon the illness being treated. Usually, the dosage will be from about 0.01 to about 10 milligrams of the peptide per kilogram of the body weight of the host animal per day. For the treatment of certain indications daily dosages up to about 100 mg/kg may be employed. The daily dosage may be given in a single dose or up to three divided doses.

As mentioned hereinbefore, CRF receptors have now been cloned and are disclosed in the aforementioned Chen et al. article, in Perrin, M., et al., *P.N.A.S*, 92, 2969–2973 (March 1995), and in Lovenberg, T., et al., *P.N.A.S.*, 92, 836–840 (January 1995). Binding affinity is a term used to refer to the strength of interaction between ligand and receptor. To demonstrate binding affinity for a CRF receptor, the peptides of the invention are easily evaluated using a tracer ligand of known affinity, such as $^{125}$I-radiolabelled oCRF, in binding assay experiments which are well known in this art. The results of such assays indicate the affinity at which each ligand binds to a CRF receptor, expressed in terms of $K_i$, an inhibitory binding affinity constant relative to such a known standard. $K_i$ (inhibitory binding affinity constant) is determined using a "standard" or "tracer" radioactive ligand and thus measures the displacement of the tracer from the receptor or binding protein; it is most properly expressed with reference to such tracer. However, so long as these assays are carefully performed under specific conditions with relatively low concentrations of receptor or the like, the calculated $K_i$ will be substantially the same as its dissociation constant $K_D$. Dissociation constant $K_D$ is representative of the concentration of ligand necessary to occupy one-half (50%) of the binding sites of a receptor or the like. It is particularly efficient to test for $K_i$ because only a single tracer need be labelled, e.g. radioiodinated. A given ligand having a high binding affinity for a CRF receptor will require the presence of very little ligand to bind at least 50% of the available binding sites so that the $K_D$ value for that ligand and receptor will be a small number. On the other hand, a given ligand having a low binding affinity for a particular CRF receptor will require the presence of a relatively high level of the ligand to bind 50% of the sites, so that the $K_D$ value for that ligand and receptor will be a large number.

With respect to a particular receptor protein, a CRF analog peptide having a $K_D$ of about 10 nM or less means that a concentration of the ligand (i.e., the CRF analog peptide) of no greater than about 10 nM will be required to occupy at least 50% of the active binding sites of the receptor protein. Such values may be fairly determined from the results obtained using a radioiodinated standard and no more than approximately 0.8 nM of the receptor (approximately 10–20 pmol receptor/mg membrane protein). Preferred peptides provided by this invention have a binding affinity ($K_D$) such that a ligand concentration of about 10 nanomolar or less is required in order to occupy (or bind to) at least 50% of the receptor binding sites, and these are considered to have high affinity. Some of these CRF analog peptides have a binding affinity of about 2 nM or less. Generally,.for purposes of this application, a dissociation constant of about 5 nanomolar or lower is considered to be an indication of strong affinity, and a $K_D$ of about 2 nanomolar or less is an indication of very strong affinity. For example, the cyclic peptide of Example 1 binds CRF-RA with very strong affinity, having a $K_D$=about 1.1 nanomolar. It is also considered to be particularly advantageous that some of the CRF analog peptides have a substantially higher affinity for one of the two families of CRF-RA and CRF-RB receptors so that they are thus selective in their biological effect.

These binding assays employing CRF receptors are straightforward to perform and can be readily carried out with initially identified or synthesized peptides to determine whether such peptides will likely be effective CRF agonists. Such binding assays can be carried out in a variety of ways as well known to one of skill in the art. A detailed example of such an assay is set forth in the Perrin, M., et al., *Endocrinology* article. Competitive binding assays employing the peptide of Example 1 B are particularly contemplated to evaluate whether candidate peptides are effective agonists with respect to each of the various CRF receptors, e.g. CRF-RA, CRF-$RB_L$ and CRF-$RB_S$ as well as assays with CRF antagonists to determine whether candidates are effective antagonists. In such assays, an appropriate CRF agonist is appropriately labeled with a substance that is readily detected, such as a radioactive isotope, e.g. $^{125}I$, or an enzyme or some other suitable tag. For example, suitably labelled cyclic CRF agonists, such as (cyclo 30-33)[$^{125}$I-D-Tyr$^3$, D-Phe$^{12}$, Nle$^{21,38}$, Glu$^{30}$, Lys$^{33}$]-r/hCRF(3-41) and its D-His$^{32}$ analog, are particularly useful tracers for use in such receptor assays. Such receptor assays can be used as screens for potential drugs which interact with CRF and/or CRF receptors.

As used herein all temperatures are °C. and all ratios are by volume. Percentages of liquid materials are also by volume. The disclosures of all U.S. patents and publications cited herein are expressly incorporated herein by reference.

Although the invention has been described with regard to its preferred embodiments, which constitute the best mode presently known to the inventor, it should be understood that various changes and modifications as would be obvious to one having the ordinary skill in this art may be made without departing from the scope of the invention which is set forth in the claims appended hereto. For example, although pharmaceutically acceptable salts and other comparable formulations are not specifically recited within the claims which follow, they are clearly equivalents thereof which include the recited peptide and are thus considered to be encompassed by such claims. Moreover, substitutions and modifications at other positions in the CRF peptide chain as indicated in the first general formula can be made without detracting from the potency of the CRF agonists. Developments to this date have shown that peptides having the specified residues at such positions in the molecule exhibit CRF activity. As a result, it is well-accepted in this art that a r/hCRF agonist (such as one having the 30-33 lactam bond described hereinbefore) will retain its improved biopotency even if multiple of the specified substitutions are incorporated. For example, D-Ala$^{31}$ can be substituted for Ala$^{31}$ with retention of biopotency well above that of the native sequence and is thus considered equivalent. Instead of D-Phe in the 12-position, L-Phe or another appropriate D-isomer generally similar to those hereinbefore mentioned, e.g. D-Cpa, may be present, and such are considered to be equivalent. The N-terminus of r/hCRF(4-41) can be extended by Glu, by Glu-Glu, or by Ser-Glu-Glu or by other suitable di- or tripeptides and/or can be acylated by an acyl group having 15 or less carbon atoms, preferably 7 or less, e.g. acetyl; the N-terminus may also be shortened by an additional 1 or 2 residues, i.e. (cyclo 30-33)[Ac-Pro$^5$, D-Phe$^{12}$, Nle$^{21,38}$, Glu$^{30}$, Lys$^{33}$]r/hCRF(5-41). Such changes are considered to produce equivalent CRF agonists. In addition, instead of the simple amide at the C-terminus, a lower alkyl-substituted amide, e.g. 1–4 carbon atoms, i.e. methylamide, ethylamide, etc, may be incorporated. As an alternative to a disulfide cyclizing bond, a carba or dicarba bond can be used (see U.S. Pat. No. 4,115,554) which is considered an equivalent bond. An equivalent lactam bond can be created by linking the side chains of Lys$^{30}$ and Glu$^{33}$; however, it is not the preferred bond. The amino group which is reacted to form the 30-33 lactam cyclizing bond or the α-amino group of one of the residues in positions 30 through 33 may be alkylated, as by adding a methyl group; such changes are considered to create equivalent cyclic peptides. Likewise when a D- or L-isomer of Amp, Aph, Iamp, Lys, Hly, Orn, Dbu, Dpr, Arg, Har or Agl is present in the 32-position, its side chain amino group may be optionally alkylated by a lower alkyl group ($C_1$ to $C_5$), e.g., methyl, ethyl, isopropyl or isobutyl. Tyr or D-Tyr can be added at the N-terminus of any of the disclosed peptides (in lieu of acetylation if acetylated) to facilitate radiolabelling. All such aforementioned equivalent peptides are considered as being within the scope of the invention.

Various features of the invention are emphasized in the claims which follow.

What is claimed is:

1. A cyclic CRF agonist peptide which binds to CRF receptors CRF-RA and CRF-RB with an affinity greater than that of r/hCRF, which peptide has the formula A-$Xaa_c$-Xaa-D-Xaa-$Xaa_c$-B-$NH_2$ wherein A is a sequence of 26 to 29 amino acid residues of the corresponding sequence of a peptide of the CRF family selected from the group consisting of residues 1-29, 2-29, 3-29 or 4-29 of mammalian and fish CRFs and fish urotensins and residues 1-28, 2-28 or 3-28 of sauvagine; $Xaa_c$ are amino acid residues the side chains of which are linked in a cyclizing bond; Xaa is a natural α-amino acid residue other than Cys; D-Xaa is a residue of a D-isomer amino acid from the group consisting of D-isomers of natural α-amino acids other than Cys and unnatural aromatic α-amino acids, and B is a sequence of the last 8 amino acid residues of the C-terminal portion of one said peptide of the CRF family, wherein A may contain D-Phe or D-Leu instead of Phe or Leu at the position spaced from D-Xaa by 19 residues and may contain D-Pro instead of Pro at the position spaced from D-Xaa by 26 or 27 residues, wherein Nle may be substituted for Met in said selected peptide sequences, and wherein the N-terminus may be acylated.

2. A CRF agonist peptide having the amino acid sequence:

(cyclo 30–33)$Y_1$—$Y_2$—Pro—Pro—Ile—Ser—Leu—Asp—Leu—

Thr-D-Phe—His—Leu—Leu—Arg—Glu—Val—Leu—Glu—Nle—

Ala—$R_{23}$—Ala—Glu—Gln—Leu—Ala—Gln—$R_{30}$—Ala—His—$R_{33}$—

Asn—Arg—Lys—Leu—Nle—Glu—Ile—Ile—$NH_2$ wherein $Y_1$ is

H or Ac; $Y_2$ = is Glu, Glu—Glu, Gln—Glu, Ser—Glu—Glu,

Ser—Gln—Glu, or des-$Y_2$; $R_{23}$ is Arg or Lys;

$R_{30}$ Glu; $R_{33}$ is Lys or Orn; wherein Tyr or D-Tyr is optionally included at the N-terminus, wherein D-Pro may be substituted for either $Pro^4$ or $Pro^5$, wherein Phe may be substituted for D-Phe, and wherein $His^{32}$ is optionally substituted by D-His, D-Amp, D-Iamp, D-Arg, D-Pal, D-Nal or a D-isomer of another natural amino acid other than Cys.

3. A CRF agonist peptide according to claim 2 having the amino acid sequence:
   (cyclo 30-33)Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu- Gln-Leu-Ala-Gln-Glu-Ala-D-His-Lys-Asn-Arg-Lys-Leu-Nle-Glu-Ile-Ile-$NH_2$.

4. A CRF agonist peptide according to claim 2 having the amino acid sequence:
   (cyclo 30-33)D-Tyr-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln- Leu-Ala-Gln-Glu-Ala-D-His-Lys-Asn-Arg-Lys-Leu-Nle-Glu-Ile-Ile-$NH_2$; or
   (cyclo 30-33)Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln- Leu-Ala-Gln-Glu-Ala-D-Arg-Lys-Asn-Arg-Lys-Leu-Nle-Glu-Ile-Ile-$NH_2$; or
   (cyclo 30-33)Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln- Leu-Ala-Gln-Glu-Ala-D-2Nal-Lys-Asn-Arg-Lys-Leu-Nle-Glu-Ile-Ile-$NH_2$.

5. A method for screening for agonists for CRF receptors, which method comprises
   carrying out a competitive binding assay with a CRF receptor, a peptide according to claim 2 which contains a label, and a candidate agonist and
   determining the ability of said candidate agonist to displace said labelled peptide.

6. A screening method according to claim 5 wherein said labelled peptide is (cyclo 30-33)D-$Tyr^3$, $Nle^{21,38}$, $Glu^{30}$, D-$His^{32}$, $Lys^{33}$-r/hCRF(3-41).

7. A CRF agonist peptide having the amino acid sequence:

(cyclo 30–33)$Y_1$—$Y_2$—Pro—Pro—$R_6$—Ser—$R_8$—Asp—Leu—$R_{11}$-

D-Phe-$R_{13}$—$R_{14}$—$R_{15}$—Arg—$R_{17}$—$R_{18}$—$R_{19}$—$R_{20}$—Nle—$R_{22}$—

$R_{23}$—$R_{24}$—$R_{25}$—$R_{26}$—$R_{27}$—$R_{28}$—$R_{29}$—$R_{30}$—$R_{31}$—$R_{32}$—$R_{33}$—

$R_{34}$—Arg—$R_{36}$—$R_{37}$—Nle—$R_{39}$—$R_{40}$—$R_{41}$—$NH_2$ wherein $Y_1$ is H or an acylating agent having up to 15 carbon atoms; $Y_2$ is Glu, Asp, Gly, Glu-Glu, Asn-Asp, Gln-Glu, pGlu-Gly, Ser-Glu-Glu, Asn-Asp-Asp, Ser-Gln-Glu, or des-$Y_2$; $R_6$ is Ile, Met or Nle; $R_8$ is Leu or Ile; $R_{11}$ is Thr or Ser; $R_{13}$ is His, Tyr or Glu; $R_{14}$ is CML or Leu; $R_{15}$ is CML or Leu; $R_{17}$ is Glu, CML, Asn or Lys; $R_{18}$ is Val, Nle or Met; $R_{19}$ is CML, Leu, Ile, Ala or Aib; $R_{20}$ is Glu, D-Glu, Cys or His; $R_{22}$ is Ala, D-Ala, Aib, Thr, Asp or Glu; $R_{23}$ is Arg, Cys, Orn or Lys; $R_{24}$ is Ala, Gln, Ile, Asn or Aib; $R_{25}$ is Asp or Glu; $R_{26}$ is Gln, Asn or Lys; $R_{27}$ is CML, Glu, Gln or Leu; $R_{28}$ is Ala, Lys, Arg or Aib; $R_{29}$ is Gln, Aib or Glu; $R_{30}$ is Glu; $R_{31}$ is Ala or Aib; $R_{32}$ is His, D-His, D-Arg, D-Amp, D-Iamp, D-2Nal, D-Glu, D-Ala or an L- or D-isomer of a natural α-amino acid other than Cys; $R_{33}$ is Lys or Orn; $R_{34}$ is Asn or Aib; $R_{36}$ is Lys, Orn, Arg, Har or Leu; $R_{37}$ is CML, Leu or Tyr; $R_{39}$ is Glu, Aib or Asp; $R_{40}$ is Ile, Aib, Thr, Glu, Ala, Val, Leu, Nle, Phe, Nva, Gly or Gln; and $R_{41}$ is Ala, Ile, Gly, Val, Leu, Nle, Phe, Nva or Gln; wherein Tyr or D-Tyr may be optionally included at the N-terminus; wherein D-Phe may be substituted by Phe, Leu, Tyr, D-Leu, D-Tyr, D-Cpa, D-Nal, D-Pal or another D-isomer α-amino acid, and wherein either $Pro^4$ or $Pro^5$ may be substituted by D-Pro; provided that cyclizing bond may exist between $R_{20}$ and $R_{23}$.

8. A CRF agonist peptide according to claim 7 having the amino acid sequence:

(cyclo 30–33)$Y_1$—$Y_2$—Pro—Pro—$R_6$—Ser—$R_8$—Asp—Leu—$R_{11}$-

D-Phe-His—Leu—Leu—Arg—Glu—$R_{18}$—Leu—$R_{20}$—Nle—$R_{22}$—

$R_{23}$—Ala—$R_{25}$—Gln—Leu—Ala—$R_{29}$—$R_{30}$—Ala—$R_{32}$—$R_{33}$—

$R_{34}$—Arg—$R_{36}$—Leu—Nle—$R_{39}$—$R_{40}$—$R_{41}$—$NH_2$ wherein $Y_1$ is H or an acylating agent having up to 7 carbon atoms; $Y_2$ is Glu, Asp, Gly, Glu-Glu, Asn-Asp, Gln-Glu, pGlu-Gly, Ser-Glu-Glu, Asn-Asp-Asp, Ser-Gln-Glu, or des-$Y_2$; $R_6$ is Ile, Met or Nle; $R_8$ is Leu or Ile; $R_{11}$ is Thr or Ser; $R_{18}$ is Val, Nle or Met; $R_{20}$ is Glu, D-Glu, Cys or His; $R_{22}$ is Ala or Thr; $R_{23}$ is Arg, Cys, Orn or Lys; $R_{25}$ is Asp or Glu; $R_{29}$ is Gln or Glu; $R_{30}$ is Glu; $R_{32}$ is His, D-His, D-Arg, D-Amp, D-Iamp, D-2Nal, D-Glu, D-Ala or Ala or a D-isomer of another natural α-amino acid other than Cys; $R_{33}$ is Lys or Orn; $R_{34}$ is Asn or Aib; $R_{36}$ is Lys or Leu; $R_{39}$ is Glu or Asp; $R_{40}$ is Ile or Glu; and $R_{41}$ is Ile or Ala; wherein Phe may be substituted for D-Phe; wherein D-Pro may be substituted for $Pro^4$ or $Pro^5$ and wherein Tyr or D-Tyr may be optionally included at the N-terminus; provided that a second cyclizing bond may exist between $R_{20}$ and $R_{23}$.

9. A peptide according to claim 8 wherein $R_{18}$ is Val, $R_{22}$ is Ala, $R_{23}$ is Arg, $R_{24}$ is Ala, $R_{25}$ is Glu, $R_{28}$ is Ala, $R_{39}$ is Glu, and $R_{41}$ is Ile.

10. A CRF agonist peptide according to claim 9 having the amino acid sequence:
    (cyclo 30-33)Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln- Leu-Ala-Gln-Glu-Ala-His-Lys-Asn-Arg-Lys-Leu-Nle-Glu-Ile-Ile-$NH_2$; or
    (cyclo 30-33)Ac-Glu-Pro-Pro-Ile-Ser-Leu-Asp-Leu-Thr-D-Phe-His-Leu-Leu-Arg-Glu-Val-Leu-Glu-Nle-Ala-Arg-Ala- Glu-Gln-Leu-Ala-Gln-Glu-Ala-His-Lys-Asn-Arg-Lys-Leu-Nle-Glu-Ile-Ile-$NH_2$; or
    (cyclo 30-33)Ac-Glu-Glu-Pro-Pro-Ile-Ser-Leu-Asp-Leu-Thr-D-Phe-His-Leu-Leu-Arg-Glu-Val-Leu-Glu-Nle-Ala-Arg-Ala- Glu-Gln-Leu-Ala-Gln-Glu-Ala-His-Lys-Asn-Arg-Lys-Leu-Nle-Glu-Ile-Ile-$NH_2$; or
    (cyclo 30-33)Ac-Ser-Glu-Glu-Pro-Pro-Ile-Ser-Leu-Asp-Leu-Thr-D-Phe-His-Leu-Leu-Arg-Glu-Val-Leu-Glu-Nle-Ala-Arg- Ala-Glu-Gln-Leu-Ala-Gln-Glu-Ala-His-Lys-Asn-Arg-Lys-Leu-Nle-Glu-Ile-Ile-$NH_2$.

11. A CRF cyclic agonist peptide according to claim 7 having the amino acid sequence:
    (cyclo 30-33)Ac-Pro-D-Pro-Ile-Ser-Ile-Asp-Leu-Thr-D-Phe-His-Leu-Leu-Arg-Asn-Nle-Ile-Glu-Nle-Ala-Arg- Asn-Glu-Asn- Gln-Arg-Glu-Glu-Ala-D-His-Lys-Asn-Arg-Lys-Tyr-Leu-Asp-Glu-Val-NH$_2$, or (cyclo 30-33)Ac-Pro-D-Pro-Ile-Ser-Ile-Asp-Leu-Ser-D-Leu-Glu-Leu-Leu-Arg-Lys-Nle-Ile-Glu-Ile-Glu-Lys-Gln-Glu-Lys- Glu-Lys-Gln-Glu-Ala-D-His-Lys-Asn-Arg-Leu-Leu-Leu-Asp-Thr-Ile-NH$_2$, or (cyclo 30-33)Ac-Pro-D-Pro-Ile-Ser-Leu-Asp-Leu-Thr-D-Phe-His-Leu-Leu-Arg-Glu-Nle-Leu-Glu-Nle-Ala-Lys-Ala-Glu-Gln- Glu-Ala-Glu-Glu-Ala-D-His-Lys-Asn-Arg-Leu-Leu-Leu-Glu-Glu-Ala-NH$_2$, or (cyclo 30-33)Ac-Pro-D-Pro-Ile-Ser-Leu-Asp-Leu-Thr-D-Phe-His-Leu-Leu-Arg-Glu-Val-Leu-Glu-Nle-Ala-Arg-Ala-Glu-Gln- Leu-Ala-Gln-Glu-Ala-D-His-Lys-Asn-Arg-Lys-Leu-Nle-Glu-Ile-Ile-NH$_2$, or (cyclo 30-33)Ac-Pro-D-Pro-Ile-Ser-Ile-Asp-Leu-Thr-D-Phe-His-Leu-Leu-Arg-Asn-Nle-Ile-Glu-Nle-Ala-Arg-Ile-Glu- Asn-Glu-Arg-Glu-Glu-Ala-D-His-Lys-Asn-Arg-Lys-Tyr-Leu-Asp-Glu-Val-NH$_2$, or (cyclo 30-33)Ac-Pro-D-Pro-Ile-Ser-Leu-Asp-Leu-Thr-D-Phe-His-Leu-Leu-Arg-Glu-Val-Leu-Glu-Nle-Thr-Lys-Ala-Asp- Gln-Leu-Ala-Gln-Glu-Ala-D-His-Lys-Asn-Arg-Lys-Leu-Nle-Asp-Ile-Ala-NH$_2$.

12. A CRF agonist peptide according to claim 8 having the amino acid sequence:

(cyclo 30-33)Y$_1$-Y$_2$-Pro-Pro-Ile-Ser-Leu-Asp-Leu-Thr-D-Phe-R$_{13}$-Leu-Leu-Arg-R$_{17}$-R$_{18}$-R$_{19}$-Glu-Nle-R$_{22}$-R$_{23}$-Ala-R$_{25}$-Gln-R$_{27}$-Ala-R$_{29}$-Glu-Ala-R$_{32}$-R$_{33}$-R$_{34}$-Arg-R$_{36}$-R$_{37}$-Nle-R$_{39}$-R$_{40}$-R$_{41}$-NH$_2$ wherein Y$_1$ is H or an acylating agent having up to 7 carbon atoms; Y$_2$ is Ser-Glu-Glu or Ser-Gln-Glu; R$_{13}$ is His or Tyr; R$_{17}$ is Glu or CML; R$_{18}$ is Val, Nle or Met; R$_{19}$ is Leu or Aib; R$_{22}$ is Ala or Thr; R$_{23}$ is Arg or Lys; R$_{25}$ is Asp or Glu; R$_{27}$ is Leu or Glu; R$_{29}$ is Gln, Aib or Glu; R$_{32}$ is His, Ala, D-His or a D-isomer of a natural α-amino acid other than Cys; R$_{33}$ is Lys or Orn; R$_{34}$ is Asn or Aib; R$_{36}$ is Lys or Leu; R$_{37}$ is CML or Leu; R$_{39}$ is Glu or Asp; R$_{40}$ is Ile or Glu; and R$_{41}$ is Ala or Ile; wherein Tyr or D-Tyr may be optionally included at the N-terminus which may be shortened by deletion of a sequence of up to 3 residues; and wherein D-Phe may be substituted by Phe, D-Tyr, D-Cpa, D-Nal or D-Pal.

13. A CRF peptide agonist according to claim 8 having the formula, or a nontoxic salt thereof:

(cyclo 30-33)Ser-R$_2$-Glu-Pro-Pro-Ile-Ser-Leu-Asp-Leu-Thr-D-Phe-His-Leu-Leu-Arg-Glu-R$_{18}$-Leu-R$_{20}$-Nle-R$_{22}$-R$_{23}$-Ala-R$_{25}$-Gln-Leu-Ala -R$_{29}$-R$_{30}$-Ala-R$_{32}$-R$_{33}$-R$_{34}$-Arg-R$_{36}$-Leu-Nle-R$_{39}$-R$_{40}$-R$_{41}$-NH$_2$ wherein R$_2$ is Glu or Gln, R$_{18}$ is Val, Nle or Met; R$_{20}$ is Glu or D-Glu; R$_{22}$ is Ala or Thr; R$_{23}$ is Arg or Lys; R$_{25}$ is Asp or Glu; R$_{29}$ is Gln or Glu; R$_{30}$ is Glu; R$_{32}$ is His or Ala; R$_{33}$ is Lys or Orn; R$_{34}$ is Asn or Aib; R$_{36}$ is Lys or Leu; R$_{39}$ is Glu or Asp; R$_{40}$ is Ile or Glu; and R$_{41}$ is Ile or Ala; and wherein the N-terminus may be acylated and/or shortened by a sequence of up to 3 residues; provided that R$_{20}$ may optionally be bonded to Lys$^{23}$.

14. A CRF agonist peptide having the amino acid sequence, or a nontoxic salt thereof:

(cyclo 30-33)Y$_1$-Y$_2$-Pro-Pro-R$_6$-Ser-R$_8$-Asp-Leu-R$_{11}$-D-Phe-R$_{13}$-R$_{14}$-R$_{15}$-Arg-R$_{17}$-R$_{18}$-R$_{19}$-R$_{20}$-R$_{21}$-R$_{22}$-R$_{23}$-R$_{24}$-R$_{25}$-R$_{26}$-R$_{27}$-R$_{28}$-R$_{29}$-R$_{30}$-R$_{31}$-R$_{32}$-R$_{33}$-R$_{34}$-Arg-R$_{36}$-R$_{37}$-Nle-R$_{39}$-R$_{40}$-R$_{41}$-NH$_2$ wherein Y$_1$ is Ac or hydrogen; Y$_2$ is Glu, Asp, Gly, Glu-Glu, Asn-Asp, Gln-Glu, pGlu-Gly, Ser-Glu-Glu, Asn-Asp-Asp, Ser-Gln-Glu, or des-Y$_2$; R$_6$ is Ile, Met or Nle; R$_8$ is Leu or Ile; R$_{11}$ is Thr or Ser; R$_{13}$ is His, Tyr or Glu; R$_{14}$ is Leu or CML; R$_{15}$ is Leu or CML; R$_{17}$ is Glu, Lys, Asn or CML; R$_{18}$ is Val, Nle or Met; R$_{19}$ is Leu, Ile or CML; R$_{20}$ is His, D-Glu, Cys or Glu; R$_{21}$ is Nle, Met or Ile; R$_{22}$ is Ala, D-Ala, Aib, Thr, Asp or Glu; R$_{23}$ is Arg, Cys, Orn or Lys; R$_{24}$ is Ala, Asn, Gln, Ile or Aib; R$_{25}$ is Asp or Glu; R$_{26}$ is Gln, Asn or Lys; R$_{27}$ is Leu, Glu, Gln or CML; R$_{28}$ is Ala, Arg, Lys or Aib; R$_{29}$ is Gln, Aib or Glu; R$_{30}$ is Glu; R$_{31}$ is Ala or Aib; R$_{32}$ is His, D-His, Aib, D-Arg, D-2Nal, D-3Pal, D-Amp, D-Iamp, Gly, Tyr, D-Tyr, Ala, D-Ala or another aromatic D-isomer α-amino acid; R$_{33}$ is Lys or Orn; R$_{34}$ is Asn or Aib; R$_{36}$ is Lys, Orn, Arg, Har or Leu; R$_{37}$ is CML, Leu or Tyr; R$_{39}$ is Glu, Aib or Asp; R$_{40}$ is Ile, Aib, Thr, Glu, Ala, Val, Leu, Nle, Phe, Nva, Gly or Gln; and R$_{41}$ is Ala, Ile, Gly, Val, Leu, Nle, Phe, Nva or Gln; wherein D-Leu or Phe or Leu may be substituted for D-Phe; wherein D-Pro may be substituted for Pro$^4$ or Pro$^5$; and wherein Tyr or D-Tyr may be optionally included at the N-terminus; provided that a second cyclizing bond may exist between R$_{20}$ and R$_{23}$.

15. A peptide according to claim 14 wherein R$_{30}$ is Glu and R$_{33}$ is Lys and wherein R$_{32}$ is D-His, D-Amp, D-Iamp, D-Tyr, D-Arg, D-Ala, D-3Pal or D-2Nal.

16. A CRF agonist peptide according to claim 14 having the amino acid sequence:

(bicyclo 20-23, 30-33)Ac-Pro-Pro-Ile-Ser-Leu-Asp-Leu-Thr-D-Phe-His-Leu-Leu-Arg-Glu-Val-Leu-Glu-Nle-Ala-Lys-Ala- Glu-Gln-Leu-Ala-Gln-Glu-Ala-His-Lys-Asn-Arg-Lys-Leu-Nle-Glu-Ile-Ile-NH$_2$ or (bicyclo 20-23, 30-33)Ac-Pro-Pro-Ile-Ser-Leu-Asp-Leu-Thr-D-Phe-His-Leu-Leu-Arg-Glu-Val-Leu-Glu-Nle-Ala-Lys-Ala- Glu-Gln-Leu-Ala-Gln-Glu-Ala-D-His-Lys-Asn-Arg-Lys-Leu-Nle-Glu-Ile-Ile-NH$_2$.

17. A CRF agonist peptide according to claim 14 having the amino acid sequence:

(cyclo 30-33)Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln- CML-Ala-Gln-Glu-Ala-D-Amp-Lys-Asn-Arg-Lys-Leu-Nle-Glu-Ile-Ile-NH$_2$ or (cyclo 30-33)Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln- CML-Ala-Gln-Glu-Ala-D-His-Lys-Asn-Arg-Lys-Leu-Nle-Glu-Ile-Ile-NH$_2$ or (cyclo 30-33)Ac-Pro-Pro-Ile-Ser-Leu-Asp-Leu-Thr-D-2Nal-His-Leu-Leu-Arg-Glu-Val-Leu-Glu-Nle-Ala-Arg-Ala-Glu- Gln-Leu-Ala-Gln-Glu-Ala-His-Lys-Asn-Arg-Lys-Leu-Nle-Glu-Ile-Ile-NH$_2$.

18. A CRF agonist peptide according to claim 15 having the amino acid sequence, or a nontoxic salt thereof:

(cyclo 30-33)Y$_1$-Y$_2$-Pro-Pro-Ile-Ser-R$_8$-Asp-Leu-R$_{11}$-R$_{12}$-R$_{13}$-Leu-Leu-Arg-R$_{17}$-R$_{18}$-R$_{19}$-Glu-R$_{21}$-R$_{22}$-R$_{23}$-R$_{24}$-Glu-R$_{26}$-R$_{27}$-R$_{28}$-R$_{29}$-Glu-Ala-R$_{32}$-Lys-Asn-Arg-R$_{36}$-R$_{37}$-R$_{38}$-R$_{39}$-R$_{40}$-R$_{41}$-NH$_2$ wherein Y$_1$ is Ac or hydrogen; Y$_2$ is Glu, Asp, Gly, Glu-Glu, Asn-Asp, Gln-Glu, pGly-Gly, Ser-Glu-Glu, Asn-Asp-Asp, Ser-Gln-Glu, or des-Y$_2$; R$_8$ is Leu or Ile; R$_{11}$ is Thr or Ser; R$_{12}$ is D-Phe or D-Leu; R$_{13}$ is His or Glu; R$_{17}$ is Glu, Lys or Asn; R$_{18}$ is Val or Nle; R$_{19}$ is Leu or Ile; R$_{21}$ is Nle or Ile; R$_{22}$ is Ala or Glu; R$_{23}$ is Arg or Lys; R$_{24}$ is Ala, Asn, Gln or Ile; R$_{26}$ is Gln, Asn or Lys; R$_{27}$ is Leu, Glu or Gln; R$_{28}$ is Ala, Arg or Lys; R$_{29}$ is Gln or Glu; R$_{32}$ is His, Gly, Ala, D-Ala, D-His or another aromatic D-isomer α-amino acid; R$_{36}$ is Lys, Arg or Leu; R$_{37}$ is Leu or Tyr; R$_{38}$ is Nle or Leu; R$_{39}$ is Glu or Asp; R$_{40}$ is Ile, Thr or Glu; and R$_{41}$ is Ala, Ile or Val; and wherein Tyr or D-Tyr may be optionally included at the N-terminus.

19. A method for screening for ligands for CRF receptors, which method comprises
carrying out a competitive binding assay with a CRF receptor, a peptide according to claim 14 which contains a label, and a candidate CRF agonist and
determining the ability of said candidte agonist to displace said labelled peptide.

20. A CRF agonist peptide according to claim 7 having the amino acid sequence:
(cyclo 30-33)Ac-Pro-Pro-Ile-Ser-Leu-Asp-Leu-Thr-D-Phe-His-Leu-Leu-Arg-Glu-Nle-Leu-Glu-Nle-Ala-Lys-Ala-Glu- Gln-Glu-Ala-Glu-Glu-Ala-D-Ala-Lys-Asn-Arg-Leu-Leu-Leu-Glu-Glu-Ala-$NH_2$; or
(cyclo 30-33)H-Asn-Asp-Asp-Pro-Pro-Ile-Ser-Ile-Asp-Leu-Thr-D-Phe-His-Leu-Leu-Arg-Asn-Nle-Ile-Glu-Nle-Ala- Arg-Ile-Glu-Asn-Glu-Arg-Glu-Glu-Ala-Gly-Lys-Asn-Arg-Lys-Tyr-Leu-Asp-Glu-Val-$NH_2$; or
(cyclo 30-33)pGlu-Gly-Pro-Pro-Ile-Ser-Ile-Asp-Leu-Ser-D-Leu-Glu-Leu-Leu-Arg-Lys-Nle-Ile-Glu-Ile-Glu-Lys-Gln-Glu- Lys-Glu-Lys-Gln-Glu-Ala-D-Ala-Lys-Asn-Arg-Leu-Leu-Leu-Asp-Thr-Ile-$NH_2$.

* * * * *

UNITED STATES PATENT AND TRADEMARK OFFICE
CERTIFICATE OF CORRECTION

PATENT NO. : 5,844,074
DATED : December 1, 1998
INVENTOR(S) : Jean E.F. Rivier

It is certified that error appears in the above-identified patent and that said Letters Patent is hereby corrected as shown below:

CLAIMS:

Column 35 (Claim 2), line 12, after "$R_{30}$", insert --is--; Column 36 (Claim 7), line 14, change "Pros" to --$Pro^5$--; Column 36 (Claim 7), line 15, after "that", insert --a second--; Column 36 (Claim 8), line 33, change "Gin" to --Gln--; Column 36 (Claim 8), line 34, change "D-lamp" to --D-Iamp--; Column 36 (Claim 10), line 45, change "9" to --8--; Column 37 (Claim 12), line 24, change "8" to --7--; Column 37 (Claim 13), line 43, change "8" to --7--; Column 38 (Claim 18), line 48, change "15" to --14-.

Signed and Sealed this

Twenty-second Day of June, 1999

Attest:

Q. TODD DICKINSON

Attesting Officer     Acting Commissioner of Patents and Trademarks